Figure 1:
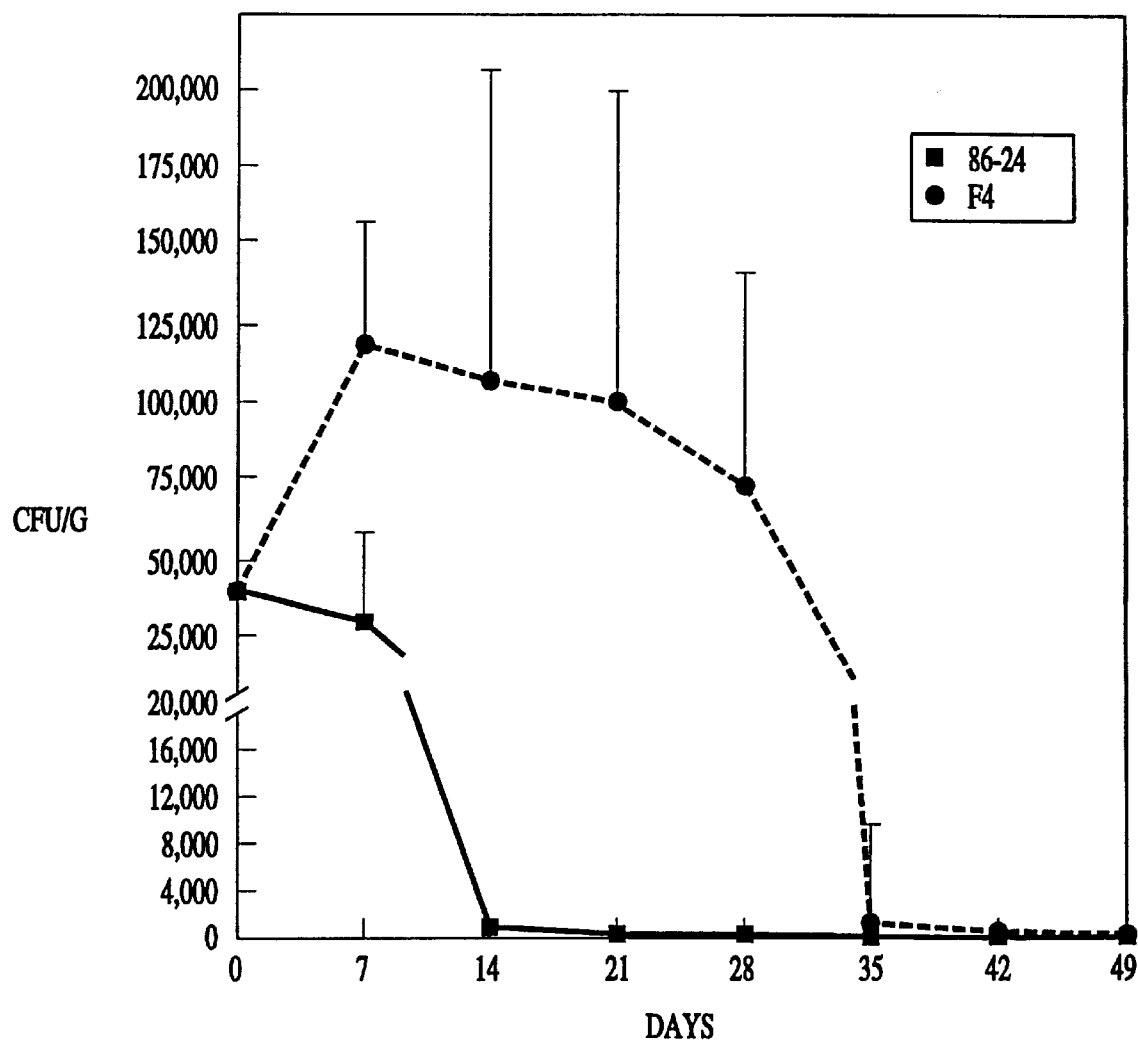

United States Patent [19]
Tarr et al.

[11] Patent Number: 6,040,421
[45] Date of Patent: Mar. 21, 2000

[54] *ESCHERICHIA COLI* O157:H7 EPITHELIAL ADHESION AND VACCINE

[75] Inventors: Phillip I. Tarr, Seattle; Sima S. Bilge, Bellevue, both of Wash.; Thomas E. Besser, Moscow, Id.; James C. Vary, Jr., Seattle, Wash.

[73] Assignees: Children's Hospital and Medical Center; University of Washington, both of Seattle; University Research Foundation, Pullman, all of Wash.

[21] Appl. No.: 09/098,082

[22] Filed: Jun. 16, 1998

Related U.S. Application Data

[60] Division of application No. 08/765,081, filed as application No. PCT/US95/06994, Jun. 7, 1995, Pat. No. 5,798,260, which is a continuation-in-part of application No. 08/265,714, Jun. 24, 1994, abandoned.

[51] Int. Cl.[7] .......................... A61K 38/00; A61K 39/02; A61K 39/108; A61K 39/00; C07C 245/00

[52] U.S. Cl. .......................... 530/300; 530/350; 530/825; 424/242.1; 424/241.1; 424/257.1; 424/185.1; 424/184.1

[58] Field of Search .............................. 424/184.1, 257.1, 424/130.1, 185.1, 242.1; 530/350, 300, 825

[56] References Cited

U.S. PATENT DOCUMENTS

| | | | |
|---|---|---|---|
| 3,975,517 | 8/1976 | Wilson | 424/87 |
| 4,443,549 | 4/1984 | Sadowski | 436/548 |
| 4,454,116 | 6/1984 | Brinton | 424/92 |
| 4,472,302 | 9/1984 | Karkhanis | 260/112 R |
| 4,652,448 | 3/1987 | Sadowski | 424/87 |
| 4,702,911 | 10/1987 | McMichael | 424/92 |
| 4,725,435 | 2/1988 | Brinton, Jr. et al. | 424/92 |
| 4,736,017 | 4/1988 | O'Hanley et al. | 530/350 |
| 4,795,803 | 1/1989 | Lindberg et al. | 530/324 |
| 5,066,596 | 11/1991 | Manning et al. | 435/252.33 |
| 5,079,165 | 1/1992 | Clements et al. | 435/252.8 |
| 5,137,721 | 8/1992 | Dallas | 424/93 A |
| 5,182,109 | 1/1993 | Tamura et al. | 424/92 |
| 5,208,024 | 5/1993 | Van Den Bosch | 424/92 |
| 5,286,484 | 2/1994 | Rodriquez et al. | 435/252.33 |
| 5,475,098 | 12/1995 | Hall et al. | 536/23.7 |
| 5,776,751 | 7/1998 | Boulton et al. | 435/194 |
| 5,834,187 | 11/1998 | Green et al. | 435/6 |
| 5,840,518 | 11/1998 | Morishita et al. | 435/69.1 |

FOREIGN PATENT DOCUMENTS

| | | |
|---|---|---|
| WO92/11354 | 7/1992 | WIPO . |
| WO94/19482 | 9/1994 | WIPO . |

OTHER PUBLICATIONS

Acres, S.D., R.W. Isaacson, L.A. Babiuk, R.A. Kapitany. Immunization of calves against enterotoxigenic colibacillosis by vaccinating dams with purification K99 antigen and whole cell bacterins. *Infect Immun* 1979; 25:121–126.

Beebakhee, G., M. Louie, J. De Azavedo, J. Brunton. Cloning and nucleotide sequence of the eae gene homologue from enterohemorrhagic *Escherichia coli* serotype O157:H7. *FEMS Microbiol Lett* 1992; 91:63–68.

Bilge, S.S., C.R. Clausen, W. Lau, S.L. Moseley. Molecular characterization of a fimbrial adhesin, F1845, mediating diffuse adherence of diarrhea–associated *Escherichia coli* to HEp–2 cells. *J Bacteriol* 1989; 171:4281–4289.

Bokete, T.N., C. M. O'Callahan, C. R. Clausen, N. M. Tang, N. Tran, S. L. Moseley, T. R. Fritsche, P. I. Tarr. Shiga–like toxin producing *Escherichia coli* in Seattle children: a prospective study. *Gastroenterology* 1993; 105:1724–1731.

Cravioto, A., A. Tello, A. Navarro, J. Ruiz, H. Villafan, F. Uribe, C. Eslava. Association of *Escherichia coli* HEp–2 adherence patterns with type and duration of diarrhea. *Lancet* 1991; 337:262–264.

Donnenberg, M.S., J.B. Kaper. Enteropathogenic *Escherichia coli*. *Infect Immun* 1992; 60:3953–3961.

Donnenberg, M.S., S. Tzipori, M.L. McKee, A.D. O'Brien, J. Alroy, J.B. Kaper. The role of the eae gene of enterohemorrhagic *Escherichia coli* in intimate attachment in vitro and in a porcine model. *J Clin Invest* 1993; 92:1418–1424.

Duchet–Suchaux, M., P. Menanteau, F.G. Van Zijderveld. Passive protection of suckling infant mice against F41–positive enterotoxigenic *Escherichia coli* strains by intravenous inoculation of the dams with monoclonal antibodies against F41. *Infect Immun* 1992; 60:2828–2834.

Dytoc, M. et al., "Multiple Determinants of Verotoxin–Producing *Escherichia coli* O157:H7 Attachment–Effacement," *Infect. Immun.* 61(8):3382–3391 (1993).

Evans, G.A., K. Lewis, B.E. Rothenberg. High efficiency vectors for cosmid microcloning and genomic analysis. *Gene* 1989; 79:9–20.

Francis, D.H., J.A. Willgohs. Evaluation of a live avirulent *Escherichia coli* vaccine for K88+, LT+ enterotoxigenic colibacillosis in weaned pigs. *Am J Vet Res* 1991; 52:1051–1055.

Fratamico, PM, Bhaduri, S, and Buchanan, RL. Studies on *Escherichia coli* serotype O157:H7 strains containing a 60–MDa plasmid and on 60–MDa plasmid–cured derivatives. *J Med Microbiol* 39:371–381, 1993.

Griffin, P.M., S.M. Ostroff, R.V. Tauxe, K.D. Greene, J.G. Wells, J.H. Lewis, P.A. Blake. Illness associated with *Escherichia coli* O157:H7 infections: a broad clinical spectrum *Ann Intern Med* 1988; 109:705–712.

(List continued on next page.)

*Primary Examiner*—James C. Housel
*Assistant Examiner*—S. Devi
*Attorney, Agent, or Firm*—Christensen O'Connor Johnson & Kindness PLLC

[57] ABSTRACT

Polypeptides encoded by a continuous segment of chromosomal DNA from *E. coli* O157:H7, isolated on plasmid pSC(overlap) (ATCC No. 69648), that encodes an adhesin (SEQ ID NO:5) that mediates bacterial colonization of bovine intestines, vaccines derived therefrom, and antibodies directed against the adhesin.

2 Claims, 2 Drawing Sheets

OTHER PUBLICATIONS

Ikemori, Y., M. Kuroki, R.C. Peralta, H. Yokoyama, Y. Kodama. Protection of neonatal calves against fatal enteric colibacillosis by administration of egg yolk powder from hens immunized with K99–piliated enterotoxigenic *Escherichia coli*. *Am J Vet Res* 1992; 53:2005–2008.

Isaacson, R.E., E.A. Dean, R.L. Morgan, H.W. Moon. Immunization of suckling pigs against enterotoxigenic *Escherichia coli*–induced diarrheal disease by vaccinating dams with purified K99 or 987P pili: antibody production in response to vaccination. *Infect Immun* 1980; 29:824–826.

Junkins, A., M.P. DoylE. comparison of adherence properties of *Escherichia coli* O157:H7 and a 60–megadalton plasmid–cured derivativE. *curr Microbiol* 1989; 19:21–27.

Karch, H., J. Hessemann, R. Laufs, A.D. O'Brien, C.O. Tacket, M.M. Levine. A plasmid of enterohemorrhagic *Escherichia coli* O157:H7 is required for expression of a new fimbrial antigen and for adhesion to epithelial cells. *Infect Immun* 1987; 55:455–461.

Kimura, A., K.T. Mountzouros, D.A. Relman, S. Falkow, J.L. Cowell. Bordetella pertussis filamentous hemagglutinin: evaluation as a protective antigen and colonization factor in a mouse respiratory infection model. *Infect Immun* 1990; 58:7–16.

Louie, M., J.C.S. deAzavedo, M.Y.C. Handelsman, C.G.Clork, A. Ally, M. Dytoc, P. Sherman, J. Brunton. Expression and characterization of the eaeA gene product of *Escherichia coli* serotype O157:H7. *Infect Immun* 61:4085–4092, 1993.

Moon, H.W., R.E. Isaacson, J. Pohlenz. Mechanisms of association of enteropathogenic *E. coli* with intestinal epithelium. *Am J Clin Nutrition* 1979; 32:119–127.

Morgan, R.L., R.E. Issacson, H.W. Moon, C.C. Brinton, C.C. To. Immunization of suckling pigs against enterotoxigenic *Escherichia coli*–induced diarrheal disease by vaccinating dams with purified 987 or K99 pili: protection correlates with pilus homology of vaccine and challenge. *Infect Immun* 1978; 22:771–777.

J.A. Morris, C. Wray, W.J. Sojka. Passive protection of lambs against enteropathogenic *Escherichia coli*: role of antibodies in the serum and colostrum of dams vaccinated with K99 antigen. *J Med Microbiol* 1980; 13:265–271.

Pecha, B., D. Low, P. O'Hanley. Gal–Gal pili vaccines prevents pyelonephritis by piliated *Escherichia coli* in a murine model. *J Clin Invest* 1989; 83:2102–2108.

Ratnam, S., S.B. March, R. Ahmed, G.S. Bezanson, S. Kasatiya. Characterization of *Escherichia coli* serotype O157:H7, *J Clin Microbiol* 1988; 26:2006–2012.

Runnels, P.L., S.L. Moseley, H.W. Moon. F41 pili as protective antigens of enterotoxigenic *Escherichia coli* that produce F41, K99, or both pilus antigens. *Infect Immun* 55:555–558, 1987.

Sherman, P., F. Cockerill III, R. Soni, J. Brunton. Outer membranes are competitive inhibitors of *Escherichia coli* O157:H7 adherence to epithelial cells. *Infect Immun* 1991; 59:890–899.

Sherman, P.M., R. Soni. Adherence of Vero cytotoxin–producing *Escherichia coli* of serotype O157:H7 to human epithelial cells in tissue culture: role of outer membranes as bacterial adhesisn. *J Med Microbiol* 1988; 26:11–17.

Sherman, P., R. Soni, M. Karmali. Attaching and effacing adherence of Vero cytotoxin–producing *Escherichia coli* to rabbit intestinal epithelium in vivo. *Infect Immun* 1988; 56:756–761.

Sojka, W.J., C. Wray, J.A. Morris. Passive protection of lambs against experimental enteric colibacillosis by colostral transfer of antibodies from K99–vaccinated ewes. *J Med Microbiol* 1978. 11:493–499.

Tarr, P.I., M.A. Neill, J. Allen, C.J. Siccardi, S.L. Watkins, R.O. Hickman. The increasing incidence of the hemolytic–uremic syndrome in King County, Washington: lack of evidence for ascertainment bias. *Am J Epidemiol* 1989; 129:582–586.

Tarr, P.I., M.A., Neill, C.R. Clausen, J.W. Newland, R.J. Neill, S.L. Moseley. Genotypic variation in pathogenic *Escherichia coli* O157:H7 isolated from patients in Washington, 1984–1987. *J Infect Dis* 1989; 159:344–347.

Tarr, P.I., M.A. Neill, C.R. Clausen, S.L. Watkins, D.L. Christie, R.O. Hickman. *Escherichia coli* O157:H7 and the hemolytic uremic syndrome: importance of early cultures in establishing the etiology. *J Infect Dis* 1990; 162:553–556.

Taylor, R.K., C. Manoil, J.J. Mekalanos. Broad–host–range vectors for delivery of TnphoA: use in genetic analysis of secreted virulence determinants of *Vibrio cholerae*. *J Bacteriol* 1989; 171:1870–1878.

Taylor, R.K., V.L. Miller, D.B. Furlong, J.J. Mekalanos. Use of phoA gene fusions to identify a pilus colonization factor coordinately regulated with cholera toxin. *Proc Natl Acad Sci USA* 1987; 84:2833–2837.

Toth, I., M.L. Cohen, H.S. Rumschlag, L.W. Riley, E.H. White, J.H. Carr, W.W. Bond, I.K. Wachsmuth. Influence of the 60–megadalton plasmid on adherence of *Escherichia coli* O157:H7 and genetic derivatives. *Infect Innum* 1990; 58:1223–1231.

Wells, J.G., B.R. Davis, I.K. Wachsmuth, L.W. Riley, R.S. Remis, R. Sokolow, G.K. Morris. Laboratory investigation of hemorrhagic colitis outbreaks associated with a rare *Escherichia coli* serotype. *J Clin Micro* 1983; 18:512–520.

Wells, J.G., L.D. Shipman, K.D. Greene, E.G. Sowers, E.G. Green, D.N. Cameron, F.P. Downes, M.L. Martin, P.M. Grifin, S.M. Ostroff, M.E. Potter, R.V. Tauxe, and I.K. Wachsmuth. Isolation of *Escherichia coli* serotype O157:H7 and other shiga–like–toxin–producing *E. coli* from dairy cattle. *J Clin Microbiol* 1991; 29:985–989.

Yokoyama, H., R.C. Peralta, R. Diaz, S. Sendo, Y. Ikemori, Y. Kodama. Passive protective effect of chicken egg yolk immunoglobulins against experimental enterotoxigenic *Escherichia coli* infection in neonatal piglets. *Infect Immun* 1992; 60:998–1007.

Yu, J., J.B. Kaper. Cloning and characterization of the eae gene of enterohaemorrhagic *Escherichia coli* O157:H7. *Mol Microbiol* 1992; 6:411–7.

Sherman, P.M. et al. "Adherence of Vero cytotoxin–producing *Escherichia coli* of serotype 0157:H7 to human epithelial cells in tissue culture: role of ourter membranes as bacterial adhesins" *Journal of Medical Microbiology* (1988), vol. 26, pp. 11–17.

ESCHERICHIA COLI O157:H7 EPITHELIAL ADHESION AND VACCINE

This application is a divisional of prior U.S. application Ser. No. 08/765,081, now U.S. Pat. No. 5,798,260 filed Mar. 26, 1997, which is a national stage application of International application No. PCT/US95/06994, filed Jun. 7, 1995, which is a continuation-in-part of U.S. application Ser. No. 08/265,714, filed Jun. 24, 1994, now abandoned.

FIELD OF THE INVENTION

The invention relates to genetic engineering and particularly to the demonstration that a contiguous segment of chromosomal DNA from *E. coli* O157:H7 encodes an adhesin that mediates colonization of the gastrointestinal tracts of bovines, and possibly humans, with *E. coli* O157:H7 and bacteria using structurally related adherence mechanisms.

BACKGROUND OF THE INVENTION

*E. coli* O157:H7 is a virulent and common foodborne pathogen. Most outbreaks, and many sporadic cases (38,42; see the appended Citations), have been attributed to food of bovine origin. Most *E. coli* O157:H7 infections are sporadic, but this organism can cause massive epidemics by contamination of ground beef (19) and water (69). *E. coli* O157:H7 is transmissible from person to person, but the disappearance of the strain which caused the massive 1993 outbreak in Washington State soon after recall of the incriminated vehicle demonstrates that ingestion of contaminated beef, and not person to person spread, is the chief source of human infection.

*E. coli* O157:H7 organism elaborates Shiga-like toxins (SLT) I and/or II. SLT I and II inhibit protein synthesis by disrupting a glycosidic bond at a specific adenine (A4324) in 28S rRNA of the 60S ribosomal subunit. SLT-producing *E. coli* (SLTEC) are ubiquitous in food (62) and animals (47). The vast majority are probably not human pathogens.

Current data suggest that *E. coli* O157:H7 is the most common and medically significant SLTEC. Only one outbreak of bloody diarrhea caused by SLTEC other than *E. coli* O157:H7 has ever been reported (11). Additionally, even when sought appropriately, non-O157:H 7 SLTEC are rarely found in stools submitted for bacterial culture in North America compared to their frequency in the environment (8,52,59). Moreover, *E. coli* O157:H7 is the predominant precipitant of the hemolytic uremic syndrome (HUS), the most important complication of enteric infection with *E. coli* O157:H7. For example, *E. coli* O157:H7 was found in 96% of HUS patients if stool was obtained within the first six days of diarrhea (72). Even though non-O157:H7 SLTEC have caused some cases of HUS in several foreign series (10,11,12,35,40), these strains have never been reported to cause HUS in the United States. These data suggest that *E. coli* O157:H7 is the most important cattle-borne human pathogen threatening the food supply of this country today.

Cattle are the only reservoir of *E. coli* O157:H7 so far identified. Approximately 1 in 200 apparently healthy northwestern United States dairy and beef cattle carry *E. coli* O157:H7, and 8 to 16% of herds have at least one infected animal (25). Similar carriage rates have been detected nationwide (26). These are probably minimum carriage rates, because the technique used to culture *E. coli* O157:H7 is relatively insensitive.

A very low inoculum of *E. coli* O157:H7 can cause human disease. Person to person spread occurs rather easily in outbreaks and among sporadic cases (5,6,60). Microbiologic analysis of the contaminated hamburger from the 1993 Western United States outbreak demonstrated that only approximately 200 *E. coli* O157:H7 were present in each of the contaminated patties (46). It is probable that the inadequate cooking that was applied reduced this concentration by at least one log, suggesting that very few *E. coli* O157:H7, perhaps in the range of 1–10 bacteria, can cause clinically apparent infection.

Data suggest that the incidence of diseases caused by *E. coli* O157:H7 has increased in the United States, independent of ascertainment bias by diagnosing physicians (44,70). Additionally, an increasing rate of antibiotic resistance in Washington State human isolates of *E. coli* O157:H7 might portend an increased prevalence of this pathogen in animals administered antibiotics. For example, before 1988, non of 56 strains of *E. coli* O157:H7 were resistant to a wide variety of antibiotics tested, whereas after 1988, 7.4% of 176 strains were resistant to the same combination of antimicrobials (streptomycin, sulfamethoxazole, and tetracycline). It is probable that the selective pressure for the acquisition of antibiotic resistance in *E. coli* O157:H7 occurred in farm animals. This emerging resistance is of considerable concern because such strains might achieve a selective advantage over other coliform bacilli in cattle given antibiotics, thereby increasing the frequency with which food of bovine origin is contaminated with this pathogen.

Because of the ease with which *E. coli* O157:H7 can cause human disease, it is crucial to reduce this pathogen in, or eliminate if from, its ecological niche, namely the gastrointestinal tracts of healthy cattle.

The molecular mechanisms used by *E. coli* O157:H7 to adhere to epithelial cells and colonize animals are poorly characterized. However, the adhesive properties of *E. coli* O157:H7 have been noted by several investigators. Most North American strains of *E. coli* O157:H7 displayed D-mannose-resistant adherence patterns to HEp-2 or Henle 407 cells (57). Most strains adhere in the form of localized microcolonies, a phenotype strongly linked to diarrhea in epidemiological studies of enteropathogenic *E. coli* (EPEC) (13,16). A 60 MDa plasmid is present in all strains of *E. coli* O157:H7, and one group associated the expression of sparse D-mannose-resistant adhesion to Henle 407 cells to the presence of this plasmid (34). Plasmid-cured *E. coli* O157:H7 expressed no fimbriae and were nonadherent, and a 60 MDa plasmid from *E. coli* O157:H7 conferred weak adherence to non-adherent *E. coli* C600. However, other investigators have shown that plasmid-less *E. coli* O157:H7 were fimbriated, whereas laboratory *E. coli* strains were not (79). furthermore, plasmid-cured *E. coli* O157:H7 adheres to epithelial cells as well or better than its parent (22,33). Only one of five adherent strains of *E. coli* O157:H7 studied by Sherman et al. (66) was fimbriated, but this fimbriated strain also agglutinated erythrocytes. The agglutination was sensitive to D-mannose, suggesting that this adherence was due to type I fimbriae. Taken together, these data suggest that an identifiable fimbrial structure is not responsible for the adherence of most *E. coli* O157:H7 to Henle 407 cells.

Outer membranes of *E. coli* O157:H7 competitively inhibit adherence to HEp-2 cells, an inhibition which is not due to H7 flagellin or O157 lipopolysaccharide (65). Adherence of *E. coli* O157:H7 to HEp-2 cells was reduced, but not abolished, by antibody to a 94 kDa outer membrane protein (64). Antibodies to enterotoxigenic *E. coli* colonization factor antigens I and II do not detect surface structures on *E. coli* O157:H7 (78). *E. coli* O157:H7 do not have sequences homologous to the EPEC adherence factor plasmid or to the diffuse adherence adhesin (71).

Some investigators have suggested that the epithelial cell adhesion of *E. coli* O157:H7 is encoded by its eae gene (17). *E. coli* O157:H7 eae is related to inv, which encodes Yersinia invasin, which also functions as an adhesin, and EPEC eae, which encodes intimin. An eae deletion mutant of *E. coli* O157:H7 neither adhered to HEp-2 cells nor caused the attaching and effacing (AE) lesion in newborn pigs (17). When deletion mutants were complemented in trans by an intact eae gene, the strain could again cause the AE lesion, but still could not adhere in vitro. However, data from other groups suggest that the eae gene product is not an adhesin for *E. coli* O157:H7. First, despite sequence homology to inv in its bacterial localization and transmembrane domains, the receptor binding domain of *E. coli* O157:H7 eae is quite dissimilar (4,82). Second, an eae insertional mutant in *E. coli* O157:H7 retained the ability to adhere to HEp-2 cells in a quantitative adherence assay (41). Third, an eae gene product does not confer adherence on nonadherent laboratory strains of *E. coli.* (Jerse, A., et al., Proc. Natl. Acad. Sci. USA 87:7839–7843, 1990) Thus, a molecule other than the eae gene product in *E. coli* O157:H7 appears to be the primary adhesin of *E. coli* O157:H7 for bovine epithelial cells, enabling this human pathogen to colonize the bovine gastrointestinal tract.

Bacterial adhesins, when used as immunogens, prevent disease or colonization of mucosal surfaces by bacteria in many animals (1,18,21,29,30,36,49,50,55,61,68,81, which are hereby incorporated by reference). The reduction of *E. coli* O157:H7 at its bovine source would enhance the microbiologic safety of food derived from cattle, and lessen the environmental biohazard risk posed by the approximately 100,000 cattle detectably infected with *E. coli* O157:H7 at any one time in the United States. The availability of antibody for passive immunization would greatly mitigate the harm engendered by outbreaks of this infection.

SUMMARY OF THE INVENTION

Transposon-mediated mutations of *E. coli* O157:H7 have been isolated that do not adhere to HeLa cells and that have lost the ability to colonize bovine intestines. A HeLa cell in vitro system has been established that provides a means of assaying variants of *E. coli* O157:H7 for their ability to colonize cattle. The gene into which the transposon inserted have been sequenced. In a separate approach, two overlapping 40 kb segments of chromosomal DNA from *E. coli* O157:H7 have been cloned that confer D-mannose resistant adherence to nonadherent strains of *E. coli.* The overlapping region has been cloned, and *E. coli* HB101 expressing this overlapping region on a plasmid (ATCC No. 69648) have acquired the ability to adhere to epithelial cells of both human (HeLa) and bovine (MDBK) origin. These findings demonstrate that a contiguous segment of chromosomal DNA from *E. coli* O157:H7 encodes an adhesin, and that this same adhesin mediates both bacterial adherence to HeLa cells.

The adhesin-encoding region of pear has been identified as the nucleotide sequence of SEQ ID NO:4. Also described are recombinant expression vectors containing the adhesin-coding region, as are bacterial cells which are transformed with the recombinant expression vector. The recombinant adhesin preferably has the amino acid sequence of SEQ ID NO:5 . Also described are immunological binding partners that bind to the recombinant adhesion. Vaccine formulations of the invention contain the recombinant adhesin encoded by a nucleic acid molecule that hybridizes under stringent conditions to the nucleotide sequence of SEQ ID NO:4.

BRIEF DESCRIPTION OF THE DRAWINGS

FIG. 1 shows shedding rates of *E. coli* O157:H7 from calves inoculated with adherent strain 86-24 and nonadherent strain F4. Bars=SE FIG. 2 is a map demonstrating overlap region between cloned regions of pSC(A-G6) and pSC(T-H12), and an adherence-conferring subclone region of the overlap, pear.

DETAILED DESCRIPTION OF THE PREFERRED EMBODIMENT

*Escherichia coli* O157:H7 causes severe and potentially fatal infections in humans, especially children. This pathogen is harbored by apparently healthy cattle. The molecular mechanisms underlying the carriage of *E. coli* O157:H7 by cattle are not understood. The invention provides an isolated adhesin that enables *E. coli* O157:H7 to adhere to epithelial cells in vitro and to colonize cattle.

Transposon-based mutants of *E. coli* O157:H7 have been identified that have lost the ability to adhere to epithelial cells. These same mutants colonize calves poorly compared to parental *E. coli* O157:H7. This finding validates the use of the HeLa cell adherence assay. Additionally, a region of the *E. coli* O157:H7 chromosome has been cloned that expresses the adhesin. This chromosomal region has been designated the epithelial adherence region (ear).

Two complementary approaches were used to identify the gene encoding the adhesin that enables *E. coli* O157:H7 to colonize bovine intestines. The first approach identified a transposon mutant of *E. coli* O157:H7 that has lost the ability to adhere to HeLa cells and that also colonizes cattle poorly. For the second approach, a segment (pear) of chromosomal DNA from *E. coli* O157:H7 was cloned which, when expressed in derivatives of nonadherent *E. coli* K12, provides these strains with the ability to adhere to HeLa cells.

Our sequence analysis demonstrates that the candidate adhesin of *E. coli* O157:H7 is a homolog of the IrgA protein in *Vibrio cholerae* (Goldberg, M. B., et al., Proc. Natl. Acad. Sci. USA 88:1125–1129, 1991). This molecule is related to the TonB dependent family of outer membrane proteins in *E. coli* (Goldberg, M. B., et al., Molecular Microbiology 6(16) :2407–2418, 1992). The DNA sequence analysis of the irgA homolog which is encoded by pear, and the homology to genes encoding IrgA and CIR, are described in the following Examples.

EXAMPLE 1

Identification of mutants that have lost the ability to adhere to HeLa cells.

A prototype adherent strain, *E. coli* O157:H7 substrain 86-24, was isolated in 1986 from a patient with hemorragic colitis whose illness was traced to ground beef the patient had consumed in a fast food restaurant (23). The transposon TnphoA was used to mutagenize substrain 86-24 according to the procedures in the appended citations 73 and 74, which are hereby incorporated by reference. TnphoA, a Tn5 derivative, carries the alkaline phosphatase gene (phoA) and inserts in random locations throughout the *E. coli* genome but only in 1–3 sites per target cell. Hence, an in-frame integration of phoA of TnphoA into regions of genes encoding an extracellular domain of a protein will result in the expression of PhoA.

PhoA-expressing TnphoA mutants of *E. coli* O157:H7 were tested in the HeLa cell assay to find nonadherent mutants. This assay is described in detail in citation 8, which is hereby incorporated by reference. Bias was avoided by coding each organism, and the examining microscopist was blinded to which samples were controls and which were mutants. EPEC strain B171 was used as the positive control for localized adherence in all experiments (58). Negative controls were nonadherent E. coli HB101 and/or NM554 (56). Besides the prototype adherent substrain of E. coli O157:H7, 6 other substrains tested adhered in a localized pattern to HeLa cells in the presence of D-mannose.

As previously reported by others (75), day to day variability in the degree of adherence of E. coli O157:H7 to HeLa cells was typically observed. However, three of 177 PhoA-expressing transconjugants screened for adherence to HeLa cells proved to be consistently nonadherent when tested in the coded assay (strains A5, F4, and N11). Strains A5, F4, and N11 retained all other phenotypic and genotypic characteristics of the parent strain of E. coli O157:H7.

Southern blot analysis determined the locations of the transposon insertions in adherent and non-adherent TnphoA mutants. DNA from strains A5, F4, and N11 and from adherent mutants H8, P11, and P12 were digested with MluI, which does not cleave DNA within TnphoA. Resulting fragments were separated in an agarose gel, transferred to Nytran, and probed with a fragment from the Tn5 central region of TnphoA. Interestingly, the results indicated that there were two TnphoA insertions in the nonadherent mutants A5 and N11, and three in F4, in apparently identical MluI bands of 23 and 16 kb length. Single integrations of TnphoA are demonstrated in each of the three adherent transconjugants. TnphoA integrated in the chromosome of strains A5, F4, and N11, and not in plasmid DNA.

EXAMPLE 2
Animal Testing

The nonadherent strain F4 and wild type E. coli O157:H7 were tested for their ability to colonize conventional Holstein calves (<1 week old). After an initial feed of colostrum, calves were placed in individual holding pens in an isolation facility, and reared on whole cow's milk with free-choice access to water, alfalfa hay, and a high protein grain mixture. It was demonstrated at the outset that the calves were not excreting E. coli O157:H7 by culturing their feces on sorbitol-MacConkey agar (SMA). Four animals received either $10^8$ adherent E. coli O157:H7 86-24 NalR or $10^9$ nonadherent mutant strain F4. In dual challenge experiments, each of four calves simultaneously received $10^8$ adherent E. coli O157:H7 86-24 and $10^9$ nonadherent TnphoA mutant F4. E. coli O157:H7 was a spontaneously nalidixic acid resistant mutant selected on agar plates containing nalidixic acid. TnphoA encodes kanamycin resistance.

The respective antibiotic resistances of these strains were exploited to identify E. coli O157:H7 in fecal samples by screening for shed challenge organisms on sorbitol MacConkey agar (SMA) containing nalidixic acid with or without kanamycin. Antibiotic resistant, sorbitol nonfermenting colonies were confirmed to be E. coli O157:H7 by their reactivity in the O157 latex particle agglutination test (Oxoid E. coli O157 Test; Unipath Limited, Hampshire, England). The nonadherent strain was detectable for fewer days and at lower concentrations as shown in FIG. 1, which summarizes the results of all challenges. The animals showed no ill effects which could be attributed to the E. coli O157:H7.

The shedding index (cfu/g of stool×number of days shed) was significantly greater for the adherent than for the non-adherent strain when analyzed by non-parametric rank sum analysis (p=0.028). Strain F4 grows as well as strain 86-24 NalR in fresh bovine stool and rumen contents, and in liquid broth, incubated aerobically overnight. These data suggest that the abbreviated excretion of the TnphoA mutant by the challenged calves is not related to decreased viability of the mutant compared to the parent strain, even though it is difficult to simulate in vitro the exact conditions of the calf gastrointestinal tract. By demonstrating that calves retain the adherent strain more effectively than the nonadherent strain, these results validate the use of the HeLa cell in vitro adhesion assay for use in development of other reagents relevant to vaccine preparation.

EXAMPLE 3
Expression of a recombinant adhesin using chromosomal DNA from E. coli O157:H7.

A segment of DNA has been derived from the chromosome of E. coli O157:H7 strain 86-24 NalR that renders nonadherent E. coli NM554 adherent. To clone this segment, approximately 2000 PhoA expressing and nonexpressing TnphoA mutants of E. coli O157:H7 86-24 NalR were screened, and one transconjugant (20D2B) was found that no longer reacted in the O157 latex particle agglutination test. This sorbitol negative mutant produced SLT II, was H7 antigen positive and β-glucuronidase negative, and possessed the same API score as the parental strain. (API score refers to a product produced by Analytab, Plainview, N.Y., which determines multiple bacterial growth characteristics. A score is given for each characteristic; taken in total, the score speciates bacteria. Within a species, there may be multiple scores.) However, 20D2B was highly adherent to HeLa cells. A partial Sau3a digest of genomic DNA of the hyperadherent strain 20D2B was ligated into plasmid Supercos (pSC) (20, 77), packaged, and used to transduce nonadherent laboratory strain NM554. This experiment yielded 2200 transductants with an average of 40 kb of DNA inserted into the BamHI site of pSC.

The 2200 cosmid clones were screened for adherence to HeLa cells, and two adherent clones were identified and designated pSC(A-G6) and pSC(T-H12). E. coli NM554 containing pSC(A-G6) and pSC(T-H12)) adhered to HeLa cells in a diffuse rather than localized pattern although nascent clusters were sometimes seen. Southern blotting demonstrated that: (a) the A-G6 and T-H12 determinants overlap by approximately 15 kb; (b) these inserts are derived from E. coli O157:H7 chromosomal DNA; (c) the inserts do not encode eae, bfp (which encodes the bundle forming pilus adhesin of EPEC), or SLT II; and (d) the overlap region is conserved in each of 9 E. coli O157:H7 tested, but not in E. coli HB101, DH5α, or EPEC B171.

Figure 2:
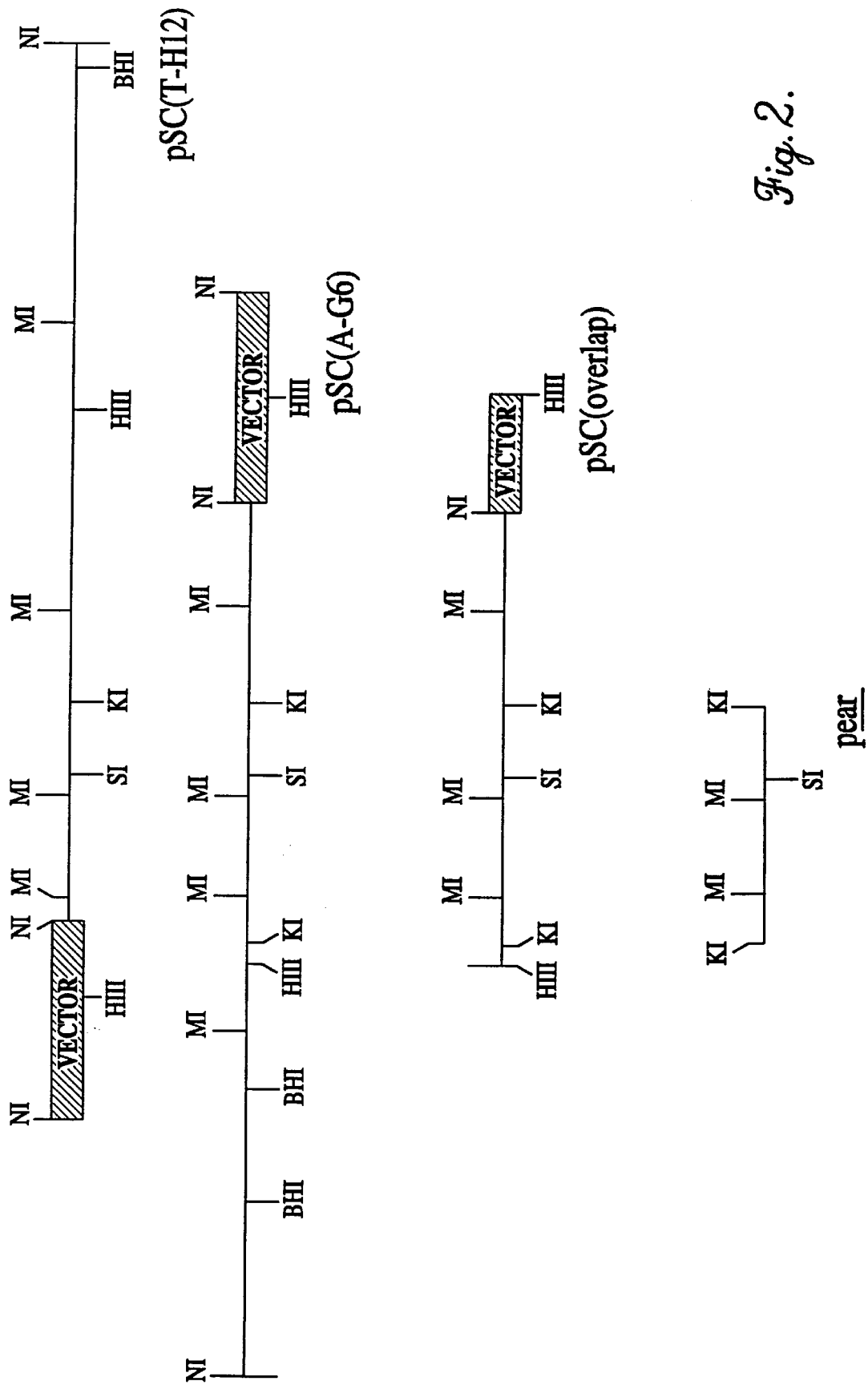

As shown in FIG. 2, a deletion mutant of pSC(A-G6), designated "pSC(overlap)" (ATCC No. 69648), retains the overlapping segment between pSC(A-G6) and pSC(T-H12). Interestingly, nonadherent E. coli HB101 transformed with pSC(overlap) display diffuse adherence to Madin-Darby bovine kidney cells (MDBK), and, in a preliminary experiment, localized adherence to HeLa cells. An 8 kb subclone of pSC(overlap), designated "pear", restores adherence to non-adherent strain A5. (pear, and the irgA homologous subclone described below, display diffuse adherence to HeLa cells.)

The data summarized above suggest that: (1) an identifiable adhesin from E. coli O157:H7 expressed in E. coli HB101 (pear) enables E. coli O157:H7 to adhere to epithelial cells of human (HeLa) and bovine (MDBK) origin in vitro; and (2) this adhesin is the same molecule which permits E. coli O157:H7 to remain in the gastrointestinal tracts of bovines. Further identification and characterization of the subject recombinant E. coli O157:H7 adhesin is described below.

EXAMPLE 4

Identification of the genes on the adherence conferring plasmid (pear).

pSC(overlap) itself consists of 4 kb of pSC DNA and approximately 15 kb of *E. coli* O157:H7 DNA. pear consists of 8 kb of chromosomal DNA plus the SK+ vector (Stratagene). To identify the adhesin expressed by pear, the entire fragment was sequenced and open reading frames were determined. The results are described below.

The appended SEQ ID NO:1 shows the 8,041 base pair nucleotide sequence of pear. Almost all of the sequence has been confirmed. Ambiguous DNA (in regions not encoding the candidate adhesin) is noted by N in the appended sequence. The pear insert contained three open reading frames (ORFs) of sufficient length to encode potential virulence or adherence factors. Two of these are homologous to genes necessary for resistance to tellurite (Jobling, MG, et al., Gene 66:245–258, 1988). These terE and terD homologs are shown in SEQ ID NO:2 and SEQ ID NO:3, corresponding respectively to nucleotides 7024-6449 and 7670-7092 of SEQ ID NO:1. The other ORF is homologous to a gene encoding a homolog of IrgA (Goldberg, MB, et al., Molecular Microbiology 6:2407–2418, 1992). This irgA homolog is shown in SEQ ID NO:4, which corresponds to nucleotides 3036-5126 of SEQ ID NO:1. IrgA is an outer membrane protein of *V. cholerae*, and is believed to be important for colonization of mice in an experimental system (Goldberg, MB, et al. Infection and Immunity, 58:55–60, 1990). The *E. coli* O157:H7 adhesin (SEQ ID NO:5) is also homologous to the *E. coli* colicin I receptor (CIR) (Griggs, D. W., et al., J. Bacteriol. 168:5343–5352, 1987). The amino acid homologies of the candidate adhesin to IrgA and to CIR are demonstrated by comparing SEQ ID NO:5 and SEQ ID NO:6, and SEQ ID NO:7, respectively.

EXAMPLE 5

Mutations in the irgA homolog, as cloned into an expression vector, lead to loss of adherence. Transposon (TnphoA) insertions in the irgA homolog of *E. coli* O157:H7 ablate adherence of laboratory strains of *E. coli* transformed with a plasmid vector into which an adherence conferring region has been inserted. We cannot state with certainty the exact site of the two TnphoA insertions which ablated adherence, but the regions of the insertions are between nucleotides 3271-3310 and 3801-3840 of SEQ ID NO:1.

EXAMPLE 6

A product of a single gene (i.e., the irgA homolog) confers adherence to nonadherent *E. coli*. We first performed PCR using as primers the sequences 5'GGGGATCCAATTCTG-GCATGCCGAGGCAGTCG3' (SEQ ID NO:8), corresponding to nucleotides 2895-2914 of SEQ ID NO:1) and 3'GGACCGCCTTGTCACCGTTGCTCTTAGATCTGG5' (SEQ ID NO:9, corresponding to nucleotides 5176-5196 of SEQ ID NO:1) from which DNA on pear was amplified. These sequences were cloned into the BamHI and XbaI sites of pSK+. We also amplified the same gene using as template DNA from *E. coli* O157:H7. In this latter case, the primers used were 5'GGAAGGATCCCCGAACACGCCATACG-GATAGCTG3' (SEQ ID NO:10, corresponding to nucleotides 2867-2890 of SEQ ID NO:1) and 3'GCAACGGT-GACGTTGAGGACCGCCAGATCTAAAGG5' (SEQ ID NO:11, corresponding to nucleotides 5159-5183 of SEQ ID NO:1). This latter PCR product was also cloned into pSK+, using the same BamHI and XbaI sites. In both cases, multiple laboratory strains of nonadherent *E. coli* were rendered adherent to HeLa cells by these cloned single genes.

EXAMPLE 7

The adherence of Δ-ear mutants to HeLa cells is diminished.

Strain F12 of *E. coli* O157:H7 is a hyperadherent mutant that has been mutated by TnphoA such that the O157 antigen is no longer expressed (Bilge, S. S., et al., Abstract B-7, American Society of Microbiology, 21–25 May 1995). F12 is probably hyperadherent because the lack of expression of the O157 antigen enables the adhesin to be more completely exposed on the bacterial cell surface.

We deleted the entire 8041 base pair KpnI—KpnI region (SEQ ID NO:1) of pear from strain F12 as follows. We cloned pear into a suicide vector, pCVD442 (Donnenberg, MS, et al., Infection and Immunity, 59:4310–7, 1991), which was then mated into strain F12 using *E. coli* SM10 lambda pir as a donor. Sucrose resistant, ampicillin sensitive strains were analyzed to find mutants with the SEQ ID NO:1 region deleted.

When the ear is deleted from strain F12, the organism was observed to be nonadherent or severely adherence deficient (1 cluster of microcolonies per 1–3 high powered fields) by an observer blinded to the identity of the F12 and the ear deletion mutant. (In comparison, the parent strain F12 displayed much higher levels of adherence to HeLa cells, approximately 0.5–1 cluster per cell.) This striking adherence deficiency could be complemented by the cloned genes of irgA from either the plasmid or the chromosome. Hence, this loss of adherence from the deletion of the ear is not caused by a polar effect of the deletion.

In summary, our data demonstrates that the PCR product of a single allele, an irgA homolog in *E. coli* O157:H7, confers an adherent phenotype when cloned into an appropriate vector and transformed into laboratory strains of *E. coli*. Tested strains include: *E. coli* NM554 (Raleigh, EA, et al, Nucleic Acids Research, 16:1563–75, 1988); *E. coli* HB101; and *E. coli* ORN172 (Woodall, LD, et al., Journal of Bacteriology 175:2770–8, 1993), which is an *E. coli* K12 strain from which genes encoding type I pili have been deleted. Our deletion mutation data confirm that the epithelial adherence region (ear) encodes an *E. coli* O157:H7 adhesin. Sequence data suggest that this adhesin is a homolog of IrgA of *V. cholerae*.

We have also performed TnphoA mutagenesis of *E. coli* O157:H7, and identified three nonadherent mutants (strains A5, F4, and N11), each of which sustained a TnphoA insertion in the same allele (SEQ ID NO:12). One of these strains, strain F4, was deficient in its ability to colonize in calves in an oral challenge experiment performed at the Washington State University in Pullman, Washington. Sequence analysis suggests that the TnphoA insertion in the same allele among the three nonadherent mutants may have taken place in the midst of a cluster of genes, at least one of which has homology to pro-secretory proteins in *Yersinia enterocolitica* (YscJ) (Michiels, T., et al, Journal of Bacteriology 173:4994–5009, 1991), *Rhizobium fredii* (Nolt) (Meinhardt, L. W., et al., Molecular Microbiology 6:2407–2418, 1992), and *Xanthomonas compestris* (HrpB) (Fenselan, S., et al., Molecular Plant-Microbe Interactions 5:390–396, 1992), and it is possible that the secretion of the *E. coli* O157:H7 adhesin is controlled by this secretory mechanism.

EXAMPLE 8

Construct recombinants and deletion mutants for bovine challenge experiments.

Our data suggest that adherence to HeLa cells by *E. coli* O157:H7 correlates with optimal colonization of calves with this organism. However, the *E. coli* O157:H7 adhesin is not closely linked to a locus mutagenized by TnphoA in nonadherent strain F4. To exclude the possibility that separate in vitro and in vivo adherence mechanisms exist for *E. coli* O157:H7, we may (1) colonize calves with a laboratory *E. coli* expressing the recombinant O157:H7 adhesin; (2) immunize animals with a recombinant adhesin and ascertain if these animals are protected from challenge with *E. coli* O157:H7; or (3) create an isogeneic deletion mutant of *E. coli* O157:H7 and determine if this strain has lost its ability to adhere to HeLa cells and to colonize calves.

EXAMPLE 9

Study adhesin deletion mutants of *E. coli* O157:H7 in calves.

We shall determine if adhesin-deletion mutants of *E. coli* O157:H7 lose the ability to colonize challenged animals in the calf model. We have demonstrated that wild type *E. coli* O157:H7 colonizes the gastrointestinal tracts of calves longer and at higher concentrations than does a nonadherent TnphoA mutant. Ideally, we would challenge calves with a laboratory strain of *E. coli* expressing the recombinant adhesin of ear, and follow excretion of this organism. However, it is very unlikely that a recombinant host strain will survive in the gastrointestinal tract of animals. For example, plasmids of enterotoxigenic *E. coli* encoding K88 (F4) or K99 (F5) pilus adhesins did not confer the ability to colonize pig small intestine when transferred to laboratory *E. coli* strain K12, despite the clearly demonstrated role of these adhesins to colonizations of the small intestines in the wild type strains (48). Therefore, we use specific deletion mutants to authenticate the role of the in vitro adhesin in the calf model.

To validate the role of the ear adhesin in bovine colonization, we created an isogeneic, in-frame deletion mutant of almost all of the irgA homolog in *E. coli* O157:H7. To do this, we cloned regions (ca. 0.45 kb) flanking the gene encoding the IrgA homolog adhesin, up to and including nucleotide 3110 at the 5' region, and nucleotide 5051 at the 3' region of the gene encoding the IrgA homolog adhesin, such that the 1941 nucleotides between nucleotides 3110 and 5051, inclusive, are deleted from this construct, corresponding to 647 amino acids. These truncated sequences of the IrgA homolog adhesin were then inserted into pCVD442, and deletion mutants of strain 86-24 NalR were identified by virtue of their ampicillin sensitivity and sucrose resistance. The deletion was confirmed in two mutants by Southern blotting using as probes the internal (i.e., deleted) portion of irgA homologs and DNA flanking the deleted sequences. The deletion mutant is termed 86-24 (Δ irgA). The parent strain (86-24 NalR) and a ten-fold excess of deletion mutant 86-24 (Δ irgA) will be fed simultaneously to cattle, and fecal excretion will be monitored by culturing stool on SMA plates containing nalidixic acid. A representative number of strains will be collected at multiple time points after challenge, until clearance of the challenge strains, or until 60 days post challenge, whichever comes first. These strains will be individually tested for the presence of the irgA deleted sequences using the polymerase chain reaction, to determine which of the strains colonizes the cattle.

In a representative experiment, animals are challenged with dual inocula (adherent and excess nonadherent deletion mutant of *E. coli* O157:H7). Based on previous challenges, we can anticipate that at least 6 calves will excrete *E. coli* O157:H7 for at least 21 days after inoculation.

Study the humoral and secretory immune response of the calves challenged with *E. coli* O157:H7 is unknown. The calf challenge experiments described above provide a model to study this response. In particular, the humoral and secretory immune response to various *E. coli* O157:H7 components, including but not limited to the recombinant adhesin, can be quantified to determine if the development of a response is correlated to the clearance of this organism from the gastrointestinal tract.

To study the immune response of the challenged bovines to *E. coli* O157:H7, serum and saliva are obtained from each calf prior to challenge and at each sampling time, and stored at −70° C. Intestinal secretions are saved at the end of the experiment, when animals are necropsied.

The humoral and secretory immune responses of the challenged bovines to *E. coli* O157:H7 proteins are studied by protein immunoblot. Outer membranes, as well as whole cell preparations, of *E. coli* O157:H7 86-24, *E. coli* NM554 pSC(A-G6), *E. coli* NM554 pSC(T-H12), and *E. coli* HB101 (pear or a derivative) are electrophoresed in adjacent lanes in 10% SDS-PAGE gels and transferred electrophoretically to nitrocellulose membranes (32). Outer membranes from nonadherent *E. coli* are included as controls. The membranes are probed with calf serum and intestinal secretions, and adherent primary antibodies are detected by murine monoclonal antibodies to bovine IgG1, IgG2, IgM, and IgA, and goat antimouse IgG coupled to horseradish peroxidase. In control blots, the monoclonal antibodies are replaced with isotype-matched monoclonal antibodies to irrelevant antigens.

Protein immunoblot studies are extended to the recombinant adhesin produced above using pGEX (67) as well as to other strains of *E. coli* O157:H7. Antibodies from calves challenged in this section are also used in an attempt to inhibit in vitro adherence of *E. coli* O157:H7 strain 86-24 and the recombinant adherent strains to epithelial cells. Finally, the recombinant adhesin is an appropriate target molecule for an enzyme-linked immunosorbent assay to quantify the magnitude of the antibody response to the adhesin in cattle challenged with *E. coli* O157:H7.

EXAMPLE 10

Immunological characterization of a recombinant *E. coli* O157:H7 adhesin.

Standard immunochemical techniques are used to determine if the cloned adhesin (SEQ ID NO:5) is the same as the adhesin used by *E. coli* O157:H7 to adhere to HeLa cells. To achieve this objective, outer membrane proteins are prepared from laboratory strain(s) expressing the recombinant adhesin (SEQ ID NO:5). These proteins are analyzed on SDS-polyacrylamide gels, and used to immunize rabbits at three one-month intervals and Holstein cows at 30 and 60 days prepartum. Rabbits are also be immunized with killed whole bacterial cell preparations. A recombinant *E. coli* NM554, which does not adhere to HeLa cells, is used as a negative control immunogen.

Decomplemented serum from immunized rabbits and cows, and whey from the milk of immunized cows, is first absorbed against *E. coli* NM554 to deplete antibodies to outer membrane proteins which are irrelevant to adherence. The absorbed sera and milk are tested against *E. coli* O157:H7 strain 86-24, as well as additional strains, using immunofluorescence and Western blotting to determine if antibody to the recombinant antigen has specific affinity for extracellular antigens or outer membrane proteins, and to determine if this antigen is conserved. Negative control antigens consist of other *E. coli,* including diarrheagenic strains, as well as other Shiga like toxin-producing *E. coli* which do not belong to serotype O157:H7. Additional negative antibody controls include preimmune serum, and serum and milk obtained from animals immunized with nonadherent recombinant *E. coli* NM554.

The function of anti-adhesin antibodies is assessed using the in vitro HeLa cell assay, adapted to quantify the numbers of bacteria adherent to the target cells. *E. coli* O157:H7, as well as adherent and nonadherent recombinant *E. coli* NM554, are incubated with immune or control sera or milk antibodies before addition to the HeLa cell culture. Antibodies remain in the adherence assay medium. Additionally used in these assays are antibodies in serum and saliva from animals challenged with oral *E. coli* O157:H7. After the appropriate incubation period, the number of bacteria adherent per cell is enumerated in multiple fields consisting of several hundred eukaryotic cells. The microscopist is blinded to the identity of the strains and antibodies.

The anti-adhesin antibodies raised and selected as described above are also useful for the diagnostic identification of *E. coli* O157:H7. So too are *E. coli* O157:H7 nucleotide sequences within or flanking the irgA homolog having the requisite specificity and sensitivity for diagnosing the presence of strain O157:H7 in feed animals, food, and humans, as determined by screening a panel of closely related bacterial strains for specificity, and a panel of *E. coli* O157:H7 for sensitivity.

EXAMPLE 11
Immunoprophylactic vaccines.

Bacterial adhesins have been used as immunogens to prevent colonization of mucosal surfaces and/or disease in multiple food and laboratory animals. An immunoprophylactic approach to the problem of *E. coli* O157:H7 carriage using a purified recombinant adhesin (ear or subclone thereof) as a vaccine is considered to be an efficient method to improve the microbiologic safety of food of bovine origin. Preparation and administration protocols for such vaccines are known in the art. See, e.g., U.S. Pat. No. 5,286,484; No. 5,208,024; No. 5,137,721; No. 5,079,165; No. 5,066,596; No. 4,795,803; No. 4,736,017; No. 4,702,911; No. 4,725,435; No. 4,454,116; and No. 3,975,517, which are incorporated by reference herein.

It is well known in the art that vaccines administered to cattle can confer immunity to bacteria that colonize the gut. For example, U.S. Pat. No. 3,975,517, describes operable methods for vaccinating cattle. Other published methods suitable for immunizing animals include: Acres et al., 25 *infection and Immunity* 121, 1979; Linggood et al., 69 *Infection and Immunity* 2828, 1992; Francis and Willgohs, 52 *Am. J. Vet. Res* 1051, 1991; Ikemori et al., 53 *Am. J. Vet. Res.* 2005, 1992; Isaacson et al., 29 *Infection and Immunity* 824, 1980; Morgan et al., 22 *Infection and Immunity* 771, 1978; Morris et al., 13 *J. Med. Microbiol.* 265, 1980; Runnels et al., 55 *Infection and Immunity* 555, 1987; Sojka et al., 11 *J. Med. Microbiol.* 493, 1978; and Yokoyama et al., 60 *Infection and Immunity* 998, 1992. Vaccines can be prepared and administered by a variety of routes, many of which are found in Harlow and Lane, *Antibodies,* 1988, which is hereby incorporated by reference.

Immunization with the ear-encoded IrgA homolog adhesin to result in decreased excretion of *E. coli* O157:H7 requires generation of immune responses with effectors in the gastrointestinal tract of adult and sub-adult cattle, the age groups which are presented for slaughter. In this age group, the presence of a functional rumen presents a major barrier to oral vaccination in a form designed to survive passage through the abomasum (the 'true' stomach), as the very large and metabolically active rumenal compartment is thought to block passage of most intact antigens to the abomasum.

Several strategies can result in immune responses in the intestine in adult ruminants. These include: the intramammary route mentioned below; parenteral (intramuscular) immunization, because the resulting antibodies are cleared from circulation into the intestine; intranasal immunization (as antigen presentation by the pharyngeal tonsils is quite effective); and the use of highly stimulating adjuvants such as ISCOMs (immune stimulating complexes such as liposome-antigen combinations) or cholera toxin b-subunit conjugates.

Types of Vaccines: Purified antigen (prepared using standard recombinant DNA methods) or whole-cell vaccines can be used to stimulate an immune response in pregnant cows, resulting in the presence of protective antibodies in the colostrum and milk produced after parturition. The milk or colostrum can be stored for later administration to newborn calves. Alternatively, protein produced from the irgA homolog can be used to raise monoclonal antibodies which then can be used directly to confer passive immunity to newborn calves. Methods for preparing monoclonal antibodies are well-known in the art, and can be found, for example, in Harlow and Lane, *Antibodies,* Cold Spring Harbor Laboratory, 1988.

Vaccines Containing Purified Antigen: Purified IrgA homolog adhesin is formulated in sesame or peanut oil, sterile aqueous solution, or other isotonic solution suitable for injection. Stabilizers such as sorbitol or gelatin may be added. The immunogenicity can be enhanced by including various immunoadjuvants in the pharmaceutical preparation. Immunoadjuvants useful for this purpose include the water-in-oil emulsion of Freund, light mineral oil (Bayol), the commercially available emulsifiers Arlacel A and Aracel C, or monophosphoryl lipid A.

Cows are inoculated subcutaneously above the left shoulder twice, approximately 3 and 6 weeks before the onset of calving.

Whole Cell Vaccines: A bacterial strain suitable for use as a whole-cell vaccine is a nonpathogenic (to animals and humans) bacterium expressing the homolog adhesin (SEQ ID NO:4). This strain can be administered orally as a live vaccine, or can be used as a killed vaccine. Oral vaccination is an efficient means for stimulating production of secretory IgA in mucosal tissues such as the internal lining of the intestinal tract. Using a killed vaccine is the safest choice, as it obviates the risk that the non-pathogenic vaccine strain will acquire virulence genes by genetic transfer from other bacteria that may be present in the gut.

Where the goal is to acquire materials suitable for providing passive immunization, another advantageous route of administration is to inject the vaccine preparation directly into the teat canal of pregnant or nursing cows. Whether administration is oral or via injection, the vaccinated animal will produce protective antibodies in her milk that will passively immunize recipient calves.

Preparation Of Formalin-Treated Vaccine: One means of vaccine preparation incorporates some of the advantages of both live and killed whole-cell vaccines. For this procedure, a bacterial strain expressing the antigenic protein is subjected to a controlled formalin treatment. A broth culture of the vaccine strain is grown to a concentration of about $10^8$ to $10^9$, then incubated under aerobic conditions for 10 to 15 hours in the presence of about 0.04% (vol/vol) formalin (0.016% wt/vol formaldehyde). Alternatively, the vaccine strain is grown on solid media, and the cells scraped off and suspended in broth medium for the formalin treatment. Formalin-treated bacteria remain viable, but optimally the proportion of colony-forming units is reduced by about 1000-fold compared with bacteria not exposed to formalin. For each batch of vaccine, plate counts are performed to ensure that the requisite proportion of bacteria have survived the formalin treatment. If necessary, the time of exposure to formalin and the percentage of formalin added to the broth are adjusted so that the plate counts of post-treatment cultures are 1000-fold reduced compared with controls. The vaccine contains the entire broth culture constituents including metabolic waste products and extracellular proteins.

Virulence of vaccine strains are tested by oral inoculation of 3 to 4 day old suckling mice with either virulent *E. coli* O157:H7 or the formalin-treated vaccine strain. Each mouse is administered about $10^6$ to $10^8$ organisms in about 0.15 ml. Mice are orally inoculated with serial dilutions of the bacteria, and survival is determined at 40 hours.

Administration Of Vaccine: For oral administration, the formalin-treated vaccine strain is packaged in enteric coated capsules that dissolve only after passing through the stomach. To achieve prophylaxis with monoclonal antibodies, the antibody can be mixed with colostrum, or any pharmaceutical carrier suitable for oral administration.

Injection: four to eight ml doses of the vaccine are administered intramuscularly or directly into the lactiferous ducts via the teat canals of two year old cows. For lactiferous duct administration, the cows are given a series of 4 to 6 ml doses at 42, 32, 22 and 12 days prior to parturition. For intramuscular vaccination, 4 ml of the formalinized culture is injected in the side of the neck 28 days before parturition, followed by 6 ml 14 days later, and 8 ml at 5 days before the expected calving day. About 1 liter of milk is collected from vaccinated and control cows seven days after parturition. Whey is prepared by centrifuging milk at 44,000 g for two hours, then collecting the supernatant. Whey is stored either in 2 ml aliquots at 4° C., stored frozen at −30° C., or stored lyophilized.

To monitor antibody production in response to the vaccine, 1 l of milk is taken from vaccinated pregnant cows on 2,3,4,7 and 14 days after calving. Whey is prepared from the milk by centrifugation and stored as described above.

Challenging Passively-Immunized Calves: To demonstrate the protective effects of whey from vaccinated teats, newborn calves separated from their mothers are fed one aliquot of post-immune whey every 8 hours for 72 hours. Control calves are fed whey from non-vaccinated cows. Six hours after being fed the first dose of whey, the calves are infected orally with broth culture containing about $10^9$–$10^{10}$ colony forming units virulent *E. coli* O157:H7 per ml. Each day after being exposed to the O157:H7, stool samples from infected calves are cultured to detect the presence or absence of *E. coli* O157:H7. Three calves from each group are sacrificed after 10 days, and their intestines examined for the presence or absence of *E. coli* O157:H7.

Mucosal Immunization: An additional route of vaccination exploits the mucosal immune system, which provides a defense against colonization of surfaces lining the gastrointestinal and respiratory systems, and relies on the induction of IgA antibodies secreted from these organs into the lumens where organisms colonize, and viable bacterial vectors which are in themselves not harmful to animals or humans, but which could be genetically engineered to express the *E. coli* O157:H7 adhesin. For a review of mucosal immunization, see: McGhee, J. R., et al., Seminars in Hematology 30 (4 suppl 4):3–12, discussion 13–15, 1993. For example, an attenuated or harmless commensal organism, including but not limited to a member of the Enterobacteriaceae, is transformed with the *E. coli* O157:H7 recombinant adhesin. This construct is administered to animals orally, or via intranasal inoculation. The efficacy of this approach is measured by assaying for specific IgA to the antigen, or by challenging vaccinated and control animals with *E. coli* O157:H7, and following excretion of this pathogen.

Immunization With Recombinant Bacterial Antigen Produced in Transgenic Plants: An alternative approach to the prevention of the carriage of *E. coli* O157:H7 by food animals, and possibly by humans, is to introduce the *E. coli* O157:H7 adhesin expressed in transgenic plants. For example, Haq et al. introduced sequences encoding *E. coli* heat-labile enterotoxin (LT-B) on an expression vector into *Agrobacterium tumifaciens*. This host bacterial strain was used to transfer the sequences encoding LT-B into tobacco (*Nicotiana tabacum* cv. Samsun) and potato (*Solanum tuberosum* variety "Frito-Lay 1607") plants, which then expressed variable amounts of these toxin antigens, as determined by immunoassay. These bacterial proteins were fed to mice, either in the form of extract of tobacco plants which expressed LT-B, or as potatoes expressing LT-B (i.e., no extract). In both cases, serum IgG and mucosal IgA responses to LT-B were elicited.

Thus, as an analogous approach in the immunization of cattle to prevent carriage of *E. coli* O157:H7, transgenic plants expressing the *E. coli* O157:H7 adhesin are fed to food animals. The response to the antigen is measured by assaying for circulating IgG and mucosal IgA antibodies specific for the *E. coli* O157:H7 adhesin. These animals could then be challenged with *E. coli* O157:H7, and excretion followed, with appropriate control animals also challenged, to determine if an immunoprotective response has been elicited. The determination of immunoprotection would be analogous to the challenge with the irgA homolog deletion mutants, but in this case, animals immunized with transgenic plants expressing the IrgA homolog adhesin, or a control (i.e., irrelevant) antigen will be challenged with nalidixic acid resistant *E. coli* O157:H7 The excretion of challenge organisms will be followed by plating stool on SMA with nalidixic acid, and the duration and level of shedding of *E. coli* O157:H7 in the two groups will be compared.

It is also contemplated that immunizing transgenic plants may be used to protect humans from infection with *E. coli* O157:H7 and related pathogens expressing the *E. coli* O157:H7 adhesin, or homologs of this adhesin. In the case of humans, IgA and IgG can be assayed to detect a humoral response to this protein, but challenge experiments cannot be performed because of the exceptional pathogenicity of *E. coli* O157:H7.

Use of a Recombinant Adhesin as a Competitive Inhibitor of *E. coli* O157:H7 in the Gastrointestinal Tracts of Food Animals and of Humans: Large quantities of recombinant adhesin expressed by plants and consumed in the diets of animals and humans may compete with wild type *E. coli* O157:H7 and related pathogenic bacteria for binding sites on the enterocyte surface. For example, animals are put on such feed in the several days or weeks prior to shipment for slaughter, provided controlled challenge experiments show that the recombinant adhesin, expressed in plants which are then fed to the animals, promotes clearance of *E. coli* O157:H7 from the gastrointestinal tract of such animals, thereby reducing the load of this pathogen that enters the production line in abattoirs. In a similar approach, children with the early stage of gastrointestinal infection with *E. coli* O157:H7 are administered these recombinant competitive inhibitors, including but not limited to the recombinant adhesin expressed on plants, to promote clearance of the organism, thereby ameliorating infection, or preventing the development of hemolytic uremic syndrome (HUS). Also, contacts of children with *E. coli* O157:H7 infection, who have yet to display symptoms, are fed recombinant adhesin, with the intent that colonization in such potential secondary cases is prevented.

The disclosed adhesin may also be used to prevent or ameliorate human infection with *E. coli* O157:H7, as well as with bacteria which use a homolog of this adhesin, with shared active sites or epitopes. As discussed above, the *E. coli* O157:H7 adhesin demonstrates striking homology to IrgA. There are domains of high degree of homology (conserved regions) interspersed with relatively nonconserved regions (variable regions). The possibility exists, therefore, that the IrgA homolog in *E. coli* O157:H7 can be used as an immunogen (vaccine) against *V. cholerae* infections. An additional possibility is that the IrgA homolog in *E. coli* O157:H7 may be a useful vaccine against the carriage of other pathogenic Enterobacteriaceae by food animals, such as diarrheagenic *E. coli* that do not belong to serogroup O157:H7.

The IrgA homologue might also be useful in the induction of protective immunity, or as a competitive inhibitor of colonization, in several additional hosts and in several additional infections. These include (1) a vaccine to prevent infections in humans caused by *E. coli* O157:7H, and diarrheagenic *E. coli*, and *V. chloerae*; (2) a vaccine to prevent carriage by cattle, and other animals destined for human food, of diarrheagenic *E. coli*; (3) a competitive inhibitor of colonizing diarrheagenic *E. coli* in food animals. To Test the efficacy of these approaches, multiple experiments are contemplated. These include (1) the administration of immune globulin (passive immunity) from donors immunized with the IrgA homolog adhesin to high risk patients (i.e., children in contact with a primary case of *E. coli* O157:H7 infection), in a placebo-controlled fashion, to determine the differences in attack rates between the two groups; (2) a vaccine formulation could be administered to human volunteers subsequently challenged with *V. chloerae*, or to patients residing in areas of high risk for infection; (3) challenge of immunized food animals with related diarrheagenic *E. coli* (i.e., not *E. coli* O157:H7) and determine if colonization can be established. The possibility also exists that animals infected with pathogenic *E. coli* sharing an IrgA-mediated adherence mechanism cause illness in the animal industry. The IrgA homolog adhesin may, in these cases, be used to diagnose, prevent, or treat the infection. In fact, we have identified pear sequences in RDEC-1 and some *E. coli* strains from calves with diarrhea.

Glossary

Glossary of abbreviations, strains, plasmids, and genes relevant to this disclosure:

| | |
|---|---|
| EPEC | enteropathogenic *E. coli* |
| MDBK | Madin-Darby bovine kidney cells |
| PhoA | alkaline phosphatase |
| PBS | phosphate-buffered saline |
| pSC | plasmid Supercos |
| PCR | polymerase chain reaction |
| SLT | Shiga-like toxins |
| SLT I | Shiga-like toxin I |
| SLT II | Shiga-like toxinII |
| SMA | sorbitol-MacConkey agar |
| XP | 5-bromo-4-chloro-3-indolylphosphate |

*E. coli* O157:H7 86-24: An SLT-II producing isolate which caused a large restaurant-associated outbreak of hemorrhagic colitis which included two deaths (23,71).

*E. coli* O157:H7 NalR: Nalidixic acid resistant adherent mutant of *E. coli* O157:H7 86-24 used in TnphoA mutagenesis. This strain adheres in a localized pattern to HeLa cells.

*E. coli* O157:H7 Strains A5, F4, N11: TnphoA mutants of *E. coli* O157:H7 86-24 NalR which express PhoA, and are non-adherent, kanamycin resistant, and ampicillin sensitive.

*E. coli* O157:H7 Strains H8, P11, P12: TnphoA mutants of *E. coli* O157:H7 86-24 NalR which are adherent, kanamycin resistant, and ampicillin sensitive.

*E. coli* 20D2B: a TnphoA mutant of *E. coli* O157:H7 NalR which is hyperadherent. This strain does not express the O157 antigen, but retains all other characteristics of the parent strain (H7 antigen positive, sorbitol nonfermenting, SLT II positive, same API score).

*E. coli* NM554: A laboratory strain *E. coli* used for cosmid cloning.

Plasmids used:

pSC(A-G6) and pSC(T-H12): overlapping cosmid clones containing 30 kb of *E. coli* O157:H7 chromosomal DNA expressed in *E. coli* NM554 which confers D-mannose-resistant adherence on this *E. coli* in a mostly diffuse pattern.

pSC(overlap): deletion mutant of pSC(A-G6) which retains 15 kb overlap region, and confers adherence to *E. coli* HB101. pSC(overlap) was deposited on Jun. 24, 1994, under accession number 69648 at the American Type Culture Collection, 10801 University Boulevard, Manassas, Va. 20110-2209, U.S.A.

pGEX: A vector which allows the expression of the IrgA homolog adhesin and a molecule which can act as a ligand for an affinity purification step (67).

pear: adherence-conferring 7 kb sublcone of pSC (overlap).

irgA: Iron regulated gene A, from *V. cholerae*. This has regions of homology to the adhesin of *E. coli* O157:H7 that was cloned and is described in this application.

CIR: *E. coli* colicin I receptor. *E. coli* outer membrane protein which also has regions of considerable homology to the described *E. coli* O157:H7 adhesin.

Strain F12: another O157 TnphoA mutant which has lost the ability to express the O157 antigen by virtue of having sustained a TnphoA insertion in the rfb locus. This strain is hyperadherent. ear deletions from F12 are considerably less adherent than the parent strain.

Strain 86-24 NalR (Δ irgA): a deletion mutant of *E. coli* O157:H7 strain 86-24 NalR, which is used in calf challenge experiments.

ear (epithelial adherence region): sublcone of 15 kb pSC(overlap) region between pSC(A-G6) and pSC(T-H12), representing approximately 7 kb of cloned *E. coli* O157:H7 chromosomal DNA which confers the adherence phenotype to nonadherent laboratory *E. coli*.

Citations

1. Acres, S. D., et al., *Infect Immun* 1979; 25:121–126.
2. Baga, M., et al., *Escherichia coli. EMBO J* 1985; 4:3887–3893.
3. Bakker, D., et al., *Escherichia coli. Mol Microbiol* 1991; 5:875–886.
4. Beebakhee, G., et al., *FEMS Microbiol Lett* 1992; 91:63–68.
5. Bell, B, personal communication.
6. Belongia, E. A., et al., *JAMA* 1993; 269:883–888.
7. Bilge, S. S., et al., *J Bacteriol* 1989; 171:4281–4289.
8. Bokete, T. N., et al., *Gastroenterology* 1993; 105:1724–1731.
9. Borczyk, A. A., et al., *Lancet* 1987; 1:98.
10. Caprioli, A, et al., *J Infect Dis* 1992; 166:154–158.
11. Caprioli, A, et al., *J Infect Dis* 1994; 169:208–211.
12. Cordovez A., et al., *J Clin Microbiol* 1992; 30:2153–2157.

13. Cravioto, A., et al., *Lancet* 1991; 337:262–264.

14. Donnenberg, M. S., et al., *Infect Immun* 1990; 58:1565–1571.

15. Donnenberg, M. S., et al., *Infect Immun* 1991; 59:4310–4317.

16. Donnenberg, M. S., et al., *Infect Immun* 1992; 60:3953–3961.

17. Donnenberg, M. S., et al., *J Clin Invest* 1993; 92:1418–1424.

18. Duchet-Suchaux, M., et al., *Infect Immun* 1992; 60:2828–2834.

19. Enteric Diseases Branch, CDC, *Morbid Mortal Wkly Rep* 1993; 42:85–86.

20. Evans, G. A., K. et al., *Gene* 1989; 79:9–20.

21. Francis, D. H., et al., *Am J Vet Res* 1991; 52:1051–1055.

22. Fratamico, PM, et al., *J Med Microbiol* 39:371–381, 1993.

23. Griffin, P. M., et al., *Ann Intern Med* 1988; 109:705–712.

24. Griffin, P. M., et al., *Epidemiol Rev* 1991; 13:60–98.

25. Hancock, D. D., et al., *Epidemiology and Infection* 113:119–207, 1994.

26. Hancock, D. D., et al., National Prevalence Study for *Escherichia coli* O157:H7 in United States Dairy Calves. Submitted.

27. Hancock, R. E. W., et al., *J Bacteriol* 1978; 136:381–90.

28. Henikoff, S., *Gene* 1984; 28:351–359.

29. Ikemori, Y., et al., *Am J Vet Res* 1992; 53:2005–2008.

30. Isaacson, R. E., et al., *Infect Immun* 1980; 29:824–826.

31. Jacobs, A. A. C., et al., *J Bacteriol* 1987; 169:735–741.

32. Johnstone, A., et al., *Immunochemistry in Practice*, 2nd Ed. Blackwell Scientific Publications, Oxford, 1987, pp 190–196.

33. Junkins, A., et al. *Curr Microbiol* 1989; 19:21–27.

34. Karch, H., et al., *Infect Immun* 1987; 55:455–461.

35. Karmali M. A., et al., *J Infect Dis* 1985; 151:775–782.

36. Kimura, A., et al., *Infect Immun* 1990; 58:7–16.

37. Krogfelt, K. A., *Rev Infect Dis* 1991; 13:721–735.

38. LeSaux, N., et al., *J Infect Dis* 1993; 176:500–502.

39. Lindberg, f., et al., *Nature* 1987; 325:84–87.

40. Lopez E. L., et al., *J Infect Dis* 1989; 160:469–475.

41. Louie, M., et al., *Infect Immun* 61:4085–4092, 1993.

42. MacDonald K. L., et al., *JAMA* 1988; 259:3567–3570.

43. Marshall, B., et al., *Proc Natl Acad Sci USA* 1990; 87:6009–6613.

44. Martin, D. L., et al., *N Engl J Med* 1990; 323:1161–1167.

45. Martin, M. L., et al., *Lancet* 1986; ii:1043.

46. McNamara, A. M., personal communication.

47. Montenegro, M. A., et al., *J Clin Microbiol* 1990; 28:1417–1421.

48. Moon, H. W., et al., *Am J Clin Nutrition* 1979; 32:119–127.

49. Morgan, R. L., et al., *Infect Immun* 1978; 22:771–777.

50. Morris, J. A., et al., *J Med Microbiol* 1980; 13:265–271.

51. Oudega, B., et al., *Antonie van Leeuwenhoek* 1988; 54:285–299.

52. Pai C. H., et al., *J Infect Dis* 1988; 157:1054–1057.

53. Pai, C. H., et al., *Infect Immun* 1986; 51:16–23.

54. Pararuchuri, D. K., et al., *Proc Natl Acad Sci USA* 1990; 87:333–337.

55. Pecha, B., et al., *J Clin Invest* 1989; 83:2102–2108.

56. Raleigh, E. A., et al., *Nucl Acid Res* 1988; 16:1563–75.

57. Ratnam, S., et al., *J Clin Microbiol* 1988; 26:2006–2012.

58. Riley, L. W., et al., *Infect Immun* 1987; 55:2052–2056.

59. Ritchie M., et al., *J Clin Microbiol* 1992:30;461–464.

60. Rowe, P. C., et al., *Epidemiol Infect* 1993; 110:9–16.

61. Runnels, P. L., et al., *Infect Immun* 55:555–558, 1987.

62. Samadpour M., et al., *Appl Environ Microbiol* 1994; in press.

63. Sancar, A., et al., *J Bacteriol* 1979; 137:692–693.

64. Sherman, P., et al., *Infect Immun* 1991; 59:890–899.

65. Sherman, P. M., et al., *J Med Microbiol* 1988; 26:11–17.

66. Sherman, P., et al., *Infect Immun* 1988; 56:756–761.

67. Smith, D. B., et al., *Gene* 1988; 67:31–40.

68. Sojka, W. J., et al., *J Med Microbiol* 1978. 11:493–499.

69. Swerdlow, D. L., et al., *Ann Intern Med* 1992; 117:812–819.

70. Tarr, P. I., et al., *Am J Epidemiol* 1989; 129:582–586.

71. Tarr, P. I., et al., *J Infect Dis* 1989; 159:344–347.

72. Tarr, P. I., et al., *J Infect Dis* 1990; 162:553–556.

73. Taylor, R. K., et al., *J Bacteriol* 1989; 171:1870–1878.

74. Taylor, R. K., et al., *Proc Natl Acad Sci USA* 1987; 84:2833–2837.

75. Toth, I., et al., *Infect Immun* 1990; 58:1223–1231.

76. Wadolkowski, E. A., et al., *Infect Immun* 1990; 58:2483–2445.

77. Wahl, G. M., et al., *Proc Natl Acad Sci USA* 1987; 84:2160–2164.

78. Wells, J. G., et al., *J Clin Micro* 1983; 18:512–520.

79. Wells, J. G., et al., *J Clin Microbiol* 1991; 29:985–989.

80. Wessels, M. R., et al., *Proc Natl Acad Sci USA* 1991; 88:8317–8321.

81. Yokoyama, H., et al., *Infect Immun* 1992; 60:998–1007.

82. Yu, J., et al., *Mol Microbiol* 1992; 6:411–7.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated peptide comprising the amino acid sequence of SEQ ID NO:5.

2. A vaccine formulation comprising an adhesin of *Escherichia coli* encoded by the nucleotide sequence of SEQ ID NO:4.

* * * * *

UNITED STATES PATENT AND TRADEMARK OFFICE
CERTIFICATE OF CORRECTION

PATENT NO.    : 6,040,421
DATED         : March 21, 2000
INVENTOR(S)   : P.I. Tarr et al.

It is certified that error appears in the above-identified patent and that said Letters Patent is hereby corrected as shown below:

Column 1,
Item [54], under title "ADHESION" should read -- ADHESIN --.
Item [73], Assignee "University Research Foundation" should read -- Washington State University Research Foundation --.
Item [56], Refs., (Other Refs., Item 27) "adhesisn" should read -- adhesins --.
Line 2, "ADHESION" should read -- ADHESIN --.
Line 5, "now U.S. Pat. No.5,798,260 filed Mar. 26, 1997" should read -- filed Mar. 26, 1997, now U.S. Pat. No.5,78,260 --

Column 2,
Item [56], Refs., (Other Refs., Item 30) "hemolyti-c-uremic" should break as follows: --hemolytic-uremic --.
Item [56], Refs., (Other Refs., Item 31) after "M.A." delete ",".
Item [56], Refs., (Other Refs., Item 35) "*Innun*" should read -- *Immun* --.
Line 16, "non" should read -- none --.

Column 9,
Line 64, after "O157:H7" insert --: The immune response of bovines to enteric colonization with *E.coli* O157:H7 --.

Column 15,
Line 20, "chloerae;" should read -- *cholerae*; --.
Line 24, "Test" should read -- test --.
Line 31, "*chloerae,* "should read -- *cholerae,* --.
Line 55, "toxinII" should read -- toxin II --.

UNITED STATES PATENT AND TRADEMARK OFFICE
CERTIFICATE OF CORRECTION

PATENT NO. : 6,040,421
DATED : March 21, 2000
INVENTOR(S) : P.I. Tarr et al.

It is certified that error appears in the above-identified patent and that said Letters Patent is hereby corrected as shown below:

Column 17,
Line 49, "f.," should read -- F., --.

Column 18,
Line 50, "58:2483-2445." should read -- 58:2438-2445. --.

Signed and Sealed this

Twenty-eighth Day of August, 2001

*Attest:*

NICHOLAS P. GODICI
*Attesting Officer*     *Acting Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 8041 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Escherichia coli O157:H7
       (B) STRAIN: 86-24 NALR (vii) IMMEDIATE SOURCE:
       (B) CLONE: pEAR (xi) SEQUENCE DESCRIPTION: SEQ ID NO:1:

```
GGTACCTGTC GCCAGTTCTC CGATCTGTTT ACCCGGGAAA TTATCTCCTA CAGCTTGTCA    60

GAAAGGTCGG TGATGGAGCA TCGNTAATAC GATGCTATAC GATGNATTCA CAGTGCCCGG   120

CCAGAGGATG CCCCGTCGCT GCATATGGAT CAGNGTTGGC AATATCGAAT TGCAGGCTAT   180

AGGCAAAGTT AANGCCCCAT GGAGTAGCAC AAAATATGCC GCACANAGGA AACGGTCTGA   240

ATAACGCAGT GATGAAGAAC TTCTTCAGCA CACTGCTAAA ACGCATAGTG ATCGAGCGCT   300

GATTCTGGCG AACAACTGAA CTAATACATC AGAATCTGCA TTATGTTAAA TAAATATAAA   360

AAGATGGTTT AAATACCCCG TTACTTGTGA CTTACACTAT ACGGTATCGC ATCGTTTAAT   420

ATTCGCACCG GCCAGATTTT TATTTCTATT AGTTGTCACA ATACTGAATG CGTACGACCA   480

CAGTATTCTG GCTCCTGTGT GGTTATGCTT TAATTCTGCG TTCCGGGCAG ATAAGCAGTT   540

GCTTGCAGGA ATCCTTCTTG TGTTAATGTC AGTTCCCCTT TTACCAGTGC TGATTTCCAC   600

ATTCCGTCCA ACAGAGCTTA TAGCCTTTCC CTGGATTATA GCATTGTCCG GCTGAAGTTC   660

TTTTTGAATA ATAATAGAAG CACTGCTGGC AGATCCAGTC CGTTTTTCAT AACCCACTGT   720

ACTGATAACC ATAATCTAAT CAGTAGAAAT TGAGTCGAAA ATAAGCACTA CTCCATACAG   780

GATAATTAGA GGTCAGTTTG ATTATTCACA ATTCATCATC AGCATTTTCT ATTTCTGACG   840

AAATCAATAT GAAAATAACC ATATATGATA ATTATTATAA TAACGGCTTT AATTGGAATA   900

CATATATTAC AACGTATTAT ATATAATTGG TATTCTGGGA ACTATATTCT CAAAATACAG   960

TAGAAACGAG GTATGTTTCT GGTGGAAAGG ACAGTGGGAT TAAAAAGTAA GAATTGATAA  1020

AAAAACGCCA GCAACACATA GTGCCGGNGG AGGGAATACC CCATGGAGAA AATGTGATGC  1080

CTAGAGCATC ATGANTATAT AATTAAAAAT AGTTAGCGTT GTCACTACTT CNACAAAAAT  1140

AATTTTCGTA GTATAGAAAG ATATTTTTAT GCATGACCTA CCTGAATTTG CTCCGGGTAG  1200

AGGTTATAAA TAAAAATTGA ATCACGACAA ACACAATATT CATAGTATGG CGATGCCTAC  1260

GCCAGCAAGA ATAGCGNCAA TAATATTGGG AATATAATAG ACACCAGACG CACAGGCATC  1320

TCACTCCTTA ACAACAACA ATCAGGATAT TTACTTTTAC CAAGCTAACT GTTTACACCC  1380

AAAGTACACA CAATTAACCA TTCAATAACA AATGNCAATA TCCATAGCCA TACGACTTTA  1440
```

```
CCTTGTAATG TTCGGTATTT CTTTATAATT ATTCTGGGAA ATCTAACATT TATTTTTAAA      1500

ATCAAATTAT CTTGTTGTTT AAAAATAAGT TCACATACTT TATCATCTTC TTCCGCCATC      1560

AACATCTCTG CATACTTAAA CATTTCAGAA CGTTCCTTTA GCACAGAAGA GTAATTATAT      1620

GTCCAGTTCC CAGGCAATAA TGCTTATGGA TATTTAATTC ATAATTTAGA GAATATTTTG      1680

CAATAATATT TGGCAGTATT CAGAAATACC TGAAAAATCA TACTATACAG CCCTAGGGAA      1740

TGGATAAAGA TTCTAACAAA GCATTTCAAC AATATATACT TGTTAAAAAT CCATATCGAA      1800

ATGCCGTTGC AGCATTAATA TATGCCTCAT TCATAAAATG TAAAAGAGCA AGCTCGTACC      1860

AGTAGGGGGG AAATTCATTG ACATGTCCTG TCAATACGTA CAGAGCCCTG CCATGCTTGC      1920

CAGCACGTAA CAATTCCGCC CCCAGTAACC AGCGTGTTCC CTGATTATTC TCAGGGTTAT      1980

ATGTTAGTAT TTTATCAATG AGTATAACGG CATCCTGATG ACGCTGTAAA TGAACATTCG      2040

CCAGAATTGC AGCATAAAGA GCGCAAATGC ATATGCCAGA TGAGCGTGAA TATCAATGAT      2100

GTCAGGAGCA TGTCAGGCAA GACGCCTGAG TTTGTTGACG TAATTTGTTT CGTTTATTTC      2160

ATCACTATCG TATGCGTCAA GAGTTTTTTC AAACTCATCC CGAAATGGGC CAAGCCTGGT      2220

TTCAGGAAAT AAGAAATACC CTTGGTTATT GTTCACTTAA AAGTATAATT TGTAATTCAA      2280

ATCCTGAGCC TGTAAAGCGG GGAGTAACAT ATTCTATTCT GAAGAGAATA AAAGTCGTGA      2340

TGCGATGTAT CAAGCCCGGA TTGTAATCCC AGATTAACAT AGATCACAAA ACAACTTATT      2400

CTTCACTAAC GTCAAGATAA ATATCGTTGT ATGCCTTATC ACGACTACGA ATACCAGCAA      2460

GATACAACTG ACATACGGAA AGATACCACG TTTTTTACTC CCGAAAATAA CGCTAAAAAG      2520

CTACTTCCCC ATCGTTTGTC CTTAGTATTG CCAGCGCCAA CAATGTGGGC TGACATGATA      2580

AAGCTGTCTA GGAAATTGTT CGCCTCCTCA GCGGACAATC CAAATGGTGA TTGTCTCTGT      2640

TAAACGTTTA TTTTGAAGGT CGACTGAATA AGGTGATGAC GCTGTAGAAT TTTTCACGTG      2700

CCACAGAATT TTGAACGCTT TCTCTTACAA TATTTCAATG TTTCTATCAG TATTCGCCGG      2760

AAGAAGTCAT CGACCAAATC ATCCCAGTCG TCTCGCATCA CTGACCATTC ATGGTTGACA      2820

TGTGGTGGAA ATCCGCTTCT ACAGTAACCA TTTTTTATTC GCAAAACCGA ACACGCCATA      2880

CGGATAGCTG TTAACTGGCA TGCCGAGGCA GTCGTTATTT ATATTTGGTT TTGTCAATAA      2940

TCTTTATTTT TTGTAAAAGG CAAATATAAA TTATTCTCAT TATTGTTTGT ATTTGTGTAT      3000

TGTCTTGCCG GTTAACATGA TCGGAGATTA GTAATATGCG AATAACCACT CTGGCTTCCG      3060

TAGTCATTCC CTGTCTCGGA TTTTCAGCCA GCAGCATAGC TGCTGCAGAG GATGTGATGA      3120

TTGTCTCGGC ATCCGGCTAT GAGAAAAAGC TGACTAACGC AGCCGCCAGT GTTTCTGTGA      3180

TTAGCCAGGA GGAATTGCAG TCCAGCCAGT ACCACGATCT GGCGGAGGCT CTGAGATCAG      3240

TAGAGGGTGT GGATGTTGAA AGTGGTACGG GTAAAACCGG AGGGCTGGAA ATCAGCATCC      3300

GAGGAATGCC AGCCAGTTAC ACGCTGATAC TGATTGATGG TGTTCGTCAG GGCGGAAGCA      3360

GTGACGTGAC TCCCAACGGT TTTTCTGCCA TGAATACCGG GTTCATGCCC CCTCTGGCCG      3420

CCATTGAGCG TATTGAGGTT ATCAGGGGGC CGATGTCCAC ACTGTATGGC TCTGATGCGA      3480

TGGGCGGTGT GGTGAATATC ATTACCAGAA AGAATGCAGA CAAATGGCTC TCTTCCGTCA      3540

ATGCAGGGCT GAATCTGCAG GAAAGCAACA ATGGGGTAA CAGCAGCCAG TTTAATTTCT      3600

GGAGCAGTGG TCCCCTTGTG GATGATTCTG TCAGCCTGCA GGTACGCGGT AGCACACAAC      3660

AGCGTCAGGG TTCATCGGTC ACATCACTGA GCGATACAGC AGGCACGCGT ATTCCTTATC      3720

CCACGGAGTC ACAGAATTAT AATCTTGGTG CACGTCTTGA CTGGAAGGCG TCGGAGCAGG      3780

ATGTGCTCTG GTTTGATATG GATACCACCC GGCAGCGTTA TGATAACCGG GATGGGCAAC      3840
```

-continued

```
TGGGGAGTCT GACGGGGGA TATGACCGGA CCCTGCGCTA TGAGCGAAAC AAAATTTCAG    3900
CTGGCTATGA TCATACTTTC ACCTTCGGAA CATGGAAATC GTATCTGAAC TGGAACGAGA    3960
CAGAAAATAA AGGTCGTGAG CTTGTACGCA GTGTACTGAA GCGCGACAAA TGGGGGCTTG    4020
CCGGTCAGCC GCGGGAGCTT AAGGAATCGA ACCTTATCCT GAATTCATTA CTGCTTACCC    4080
CTCTGGGAGA ATCTCATCTG GTTACGGTGG GGGGCGAGTT TCAGAGCTCG TCCATGAAAG    4140
ACGGAGTTGT CCTTGCCAGC ACAGGTGAAA CTTTCCGGCA GAAAAGCTGG TCGGTATTTG    4200
CTGAGGATGA GTGGCATCTC ACGGATGCAC TTGCGCTGAC TGCGGGCAGC CGCTATGAAC    4260
ATCATGAGCA ATTCGGGGGA CACTTCAGTC CGCGTGCATA TCTGGTCTGG GATGTGGCAG    4320
ATGCCTGGAC GCTGAAAGGC GGTGTGACCA CGGGATATAA GGCACCCAGA ATGGGGCAGC    4380
TACATAAAGG GATTAGTGGT GTGTCCGGGC AGGGAAAAAC AAATCTACTT GGTAACCCCG    4440
ACCTGAAGCC GGAAGAGAGC GTCAGTTATG AGGCTGGGGT GTATTACGAT AACCCCGCCG    4500
GTCTGAATGC CAATGTCACA GGTTTTATGA CTGACTTCTC CAACAAGATT GTCTCTTATT    4560
CCATAAATGA TAACACCAAT AGCTATGTAA ACAGCGGAAA GGCCCGGTTG CACGGTGTGG    4620
AATTTGCCGG CACATTGCCG CTGTGGTCAG AGGATGTCAC GCTGTCACTG AATTACACCT    4680
GGACCCGAAG TGAACAACGT GATGGTGATA ACAAAGGTGC GCCGCTGAGT TATACCCCTG    4740
AACACATGGT GAATGCGAAA CTGAACTGGC AGATCACCGA AGAGGTGGCA TCATGGCTGG    4800
GTGCCCGTTA TCGCGGGAAA ACACCACGTT TCACCCAGAA TTATTCGTCA CTGAGCGCTG    4860
TACAGAAGAA AGTGTATGAT GAGAAAGGAG AATACCTGAA AGCCTGGACG GTGGTGGATG    4920
CAGGTCTGTC GTGGAAGATG ACGGATGCCC TGACGCTGAA TGCTGCGGTG AATAACCTGC    4980
TCAACAAGGA TTACAGTGAC GTGAGCCTGT ACAGTGCCGG TAAGAGTACG CTGTATGCCG    5040
GTGATTACTT CCAGACGGGA TCATCAACAA CAGGATATGT GATACCTGAG CGAAATTACT    5100
GGATGTCGCT GAACTATCAG TTCTGATAAT AACAAAACGC TATCACTGAC GGTAGAATAC    5160
GTTGCCACTG CAACTCCTGG CGGAACAGTG GCAACGTNTT AGGTTAAGTG CATTTCCGAT    5220
CCGCTAATGA GATTTCGTTA CCAACAACTA ATATCGTCAC AGGAAATGCA CGGATTATTT    5280
TTAACTTATC ATTTACATAC TTGTCCAGAG TGTNAGCGCA CCGCGACGGA CGTGGGGTAA    5340
AAATTAGTTT ACAGAGAGAG TGACGTTCCA GGGGAACAAC TCTTTCATGC GGTTGGCAGG    5400
CCAGGTGTTG GTTACACTGA TCACGTGGGC GTTGGCCACG TTTCCGGNTC GATTCCGTTA    5460
AGTTTTGGAG CTACCGATCA GGCTGTACAT CACTGNCGCA CTATCGCTCG TCATCTCAAA    5520
GTCCTGTCTC GTCAGCAGGA AGGTATCATT CTCTCCCGCC ATTTTTCCAG GGNCCGGTC    5580
AGATAAGTCC CTTTGTCTAT CGCTGACTCC TGACTCATAA CCCGGTTAGC AGAATGCAGG    5640
NTCACCACTC GCCACGACCA AATCCAAATA AGTCAATTGC ACCTTCTCAA TCGCCATTTT    5700
GTCAGTAAGC GTACAGCCTC AACTGATGGT ATCTTCACCA TCAATGACAA CGGTGATCGC    5760
AATTTTACTG ACGTTCGCCG GAACACGATC CAGTGCTATC TCAATGCTGG CCTGCTGCGA    5820
ACCGGTAACG AGCCTGACTG CCCCCTCAGG AGAAGACAAA TTATTATAAA AGATAAAGTC    5880
AGAATCGCCA CTGACCTTTC CCTGAGCATT AAGCATGAAC AGGGAGGTAT CGGGTTCGCC    5940
TTAAAAGCCG GATTTGNCAG GGTACTGAAG ATTCAGCCTG ATCGNAGATT GCTGAAGGGG    6000
TATGTATTGT CCGGATTGTA AATTCATATT AACTCTCCTG ATTTNTGATT ATTATTAATG    6060
CGCAGCGTTT ATATATGTTC CCTAGGCTTA GTTCTGGACG CTGGATATTC GGTGAGGCGT    6120
AAATATGGTA TGACACCATT TTTCATAACG CTGAAGTTTC TATACCTGTT GAATTTGAAT    6180
```

```
TTTCATTGAC CGGGTATCTT ATTTTCCAGG GCCCGTTCCT TCATAAGTCG CAAAAGTAAC    6240

ATATATCCGA AGGGCATGCT GTTGATATCA GACACGGAAT ACTGGCTTTA ACCAGCAACC    6300

ACAGATAAAC CCGGGGCCTG CATAAAAGGT TCATGCCAGA ATTAACATAG CTCTGCTTTC    6360

TGCCCCCCCC TTTCCCATAT TCACCCGTTG ATAGCGGATC GATACCCAAA AAAAACCCCG    6420

GCATTGCCGG GGTCAGACTC AGCGTCTTTT AGACATTGAC GCCGTGCTGG GAAGCAAGCG    6480

CTGACAGACC ACCGGCAAAA CNCTGGCCAA CAGCTTTAAA CTTCCACTCA GTACCATGGC    6540

GATACAGTTC ACCGAAGACC ATTGCGGTTT CGGTTGAGGC GTCTTCAGAC AGATCGAAAC    6600

GGGCAATTTC CGTCCCGTTG TCGTTGTTGT AAACGCGCAT GAAGCTGTTG CTCACCATGC    6660

CGAAGTTTTG TTTACGCGCT TCTGCATCAT AGATGGTAAC GGCAAATACC AGTTTTTTGA    6720

TGTCTGCTGA GACTTTGGTC AGATCGATTT TGACCTGCTC ATCGTCGCCG TCGCCTTCAC    6780

CGGTACGGTT GTCGCCCTGG TGCTCTACTG CGCCATCAGG GCTGGTTTTA TTATTGAAGA    6840

AAATGAAATG GGCATCTGAC AGTACTTTAC CGTCTTCACC TACTGCGAAT ACGGAAGCGT    6900

CCAGANCAAA ACCCTGACCA TCGGTTACAC GGGCATCCCA GCCCAGGCCA ACCATAGCGA    6960

CATTCATGGT TGGTGCTTCT TTGGTCAGAG ATACGTTGCC GCCTTTTACG AGAGAAACTG    7020

CCATTTTTAG CTCCTGCAAA CAGNTGAATG AGGCTGAATA ACACCCCCAG AAATGAAAAG    7080

TTACTTTTCG ATCAGGACGC GTTAATNCCG TACTGAGCAC ATACAGATGC CAGACCACCA    7140

GCATAACNCT GTNCTACTGC GCGGAATTTC CACTCACCAT TGTGGCGAGA CAGCTCGCCG    7200

CGCAGCATGG CAGTCTCAGT GGACGCATCT TCGGTCAGAT CGTAGCGAGC GACTTCAGTC    7260

TGGTTATCGT CATTAACCAG ACGAATAAAC GCACCGGATA CCTGACCACA GCTCTGGCGA    7320

CGAGCCTGAG CATCGTGGAT GGTCACAACG AAGATGATCT TGTCAACTTC AGACGGGACG    7380

GCGTCCAGTT TAATTTTCAG CGATTCATCA TCACCATCGC CCTCACCGGT GCGGTTATCG    7440

CCGGTGTGCG TTACGGAACC GTCGGATGAC GTCAGGTTGT TATAGAAGAT GAAATCTGAA    7500

TCGCCGCGCA CTTTGCCGTT TGAGGCCAGC AGGAATGCTG AAGCATCCAG GTCAAAGTCC    7560

TGACCGTCTG TTGAACGCGC ATCCCAGCCA AGGCCCACCA GGACATTTTT CATTGACGGA    7620

GCTGCTTTAC TCAGGGAGAC GTTCCCGCCT GTGGAAAGAG AAACACTCAT AAAATACCCT    7680

CTTCGATTAG TAATTGTTCA GGTTAACACT TAAGGGGATT ATCTCCCCTT TTCCTCAGAT    7740

TCAGGTGTGC CCGGGAACAT GACGCTTGCG AGAATGCCCA GCGCCAGTAC ACCCAGTACA    7800

ACATACAGGC TGGTTGTTGC CGCGATGCTG TAACCATGAT GCCAGATGTG ATCGATCGCA    7860

TTCAGGCCGA GTTTTGCCAC GATGAAGAAC AGCANCACGA TAGCGGCCTT CTCCAGATGN    7920

ACCAGGTNCT GTTTCAGTGC CTCNAGGACA AAATACAGAG TACGCAGACC CAGGATAGCA    7980

AACATCATGG CACTATAGAC GATGAAGCGG TTCACGACTG ACGGCAATGA TTTCCGGTAC    8040

C                                                                   8041
```

(2) INFORMATION FOR SEQ ID NO:2:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: Corresponds to complementary strand of
            SEQ ID NO:1, nucleotides 7024-6449

(iii) HYPOTHETICAL: NO (iv) ANTI-SENSE: NO (vi) ORIGINAL SOURCE:
  (A) ORGANISM: Escherichia coli O157:H7
  (B) STRAIN: 86-24 NALR (xi) SEQUENCE DESCRIPTION: SEQ ID NO:2:

| | | | | | |
|---|---|---|---|---|---|
| ATGGCAGTTT | CTCTCGTAAA | AGGCGGCAAC | GTATCTCTGA | CCAAAGAAGC | ACCAACCATG | 60 |
| AATGTCGCTA | TGGTTGGCCT | GGGCTGGGAT | GCCCGTGTAA | CCGATGGTCA | GGGTTTTGTC | 120 |
| TGGACGCTTC | CGTATTCGCA | GTAGGTGAAG | ACGGTAAAGT | ACTGTCAGAT | GCCCATTTCA | 180 |
| TTTTCTTCAA | TAATAAAACC | AGCCCTGATG | GCGCAGTAGA | GCACCAGGGC | GACAACCGTA | 240 |
| CCGGTGAAGG | CGACGGCGAC | GATGAGCAGG | TCAAAATCGA | TCTGACCAAA | GTCTCAGCAG | 300 |
| ACATCAAAAA | ACTGGTATTT | GCCGTTACCA | TCTATGATGC | AGAAGCGCGT | AAACAAAACT | 360 |
| TCGGCATGGT | GAGCAACAGC | TTCATGCGCG | TTTACAACAA | CGACAACGGG | ACGGAAATTG | 420 |
| CCCGTTTCGA | TCTGTCTGAA | GACGCCTCAA | CCGAAACCGC | AATGGTCTTC | GGTGAACTGT | 480 |
| ATCGCCATGG | TACTGAGTGG | AAGTTTAAAG | CTGTTGGCCA | GGTTTTGCCG | GTGGTCTGTC | 540 |
| AGCGCTTGCT | TCCCAGCACG | GCGTCAATGT | CTAA | | | 574 |

(2) INFORMATION FOR SEQ ID NO:3:

(i) SEQUENCE CHARACTERISTICS:
    (A) LENGTH: 576 base pairs
    (B) TYPE: nucleic acid
    (C) STRANDEDNESS: single
    (D) TOPOLOGY: linear (ii) MOLECULE TYPE: DNA (genomic)
    (A) DESCRIPTION: Corresponds to complementary strand of
        SEQ ID NO:1, nucleotides 7670-7092

(iii) HYPOTHETICAL: NO (iv) ANTI-SENSE: NO (vi) ORIGINAL SOURCE:
    (A) ORGANISM: Escherichia coli O157:H7
    (B) STRAIN: 86-24 NALR (xi) SEQUENCE DESCRIPTION: SEQ ID NO:3:

| | | | | | |
|---|---|---|---|---|---|
| ATGAGTGTTT | CTCTTTCCAC | AGGCGGGAAC | GTCTCCCTGA | GTAAAGCAGC | TCCGTCAATG | 60 |
| AAAAATGTCC | TGGTGGGCCT | TGGCTGGGAT | GCGCGTTCAA | CAGACGGTCA | GGACTTTGAC | 120 |
| CTGGATGCTT | CAGCATTCCT | GCTGGCCTCA | AACGGCAAAG | TGCGCGGCGA | TTCAGATTTC | 180 |
| ATCTTCTATA | CAACCTGAC | GTCATCCGAC | GGTTCCGTAA | CGCACACCGG | CGATAACCGC | 240 |
| ACCGGTGAGG | GCGATGGTGA | TGATGAATCG | CTGAAAATTA | AACTGGACGC | CGTCCCGTCT | 300 |
| GAAGTTGACA | AGATCATCTT | CGTTGTGACC | ATCCACGATG | CTCAGGCTCG | TCGCCAGAGC | 360 |
| TGTGGTCAGG | TATCCGGTGC | GTTTATTCGT | CTGGTTAATG | ACGATAACCA | GACTGAAGTC | 420 |
| GCTCGCTACG | ATCTGACCGA | AGATGCGTCC | ACTGAGACTG | CCATGCTGCG | CGGCGAGCTG | 480 |
| TCTCGCCACA | ATGGTGAGTG | GAAATTCCGC | GCAGTAGACA | GGTTATGCTG | GTGGTCTGGC | 540 |
| ATCTGTATGT | GCTCAGTACG | GATTAACGCG | TCCTGA | | | 576 |

(2) INFORMATION FOR SEQ ID NO:4:

(i) SEQUENCE CHARACTERISTICS:
    (A) LENGTH: 2091 base pairs
    (B) TYPE: nucleic acid
    (C) STRANDEDNESS: single
    (D) TOPOLOGY: linear (ii) MOLECULE TYPE: DNA (genomic)
            (A) DESCRIPTION: Corresponds to SEQ ID NO:1,
                nucleotides 3036-5126

(iii) HYPOTHETICAL: NO (iv) ANTI-SENSE: NO (vi) ORIGINAL SOURCE:
            (A) ORGANISM: Escherichia coli O157: H7
            (B) STRAIN: 86-24 NALR (ix) FEATURE:
            (A) NAME/KEY: CDS
            (B) LOCATION: 1..2088

(xi) SEQUENCE DESCRIPTION: SEQ ID NO:4:

```
ATG CGA ATA ACC ACT CTG GCT TCC GTA GTC ATT CCC TGT CTC GGA TTT      48
Met Arg Ile Thr Thr Leu Ala Ser Val Val Ile Pro Cys Leu Gly Phe
 1               5                  10                  15

TCA GCC AGC AGC ATA GCT GCT GCA GAG GAT GTG ATG ATT GTC TCG GCA      96
Ser Ala Ser Ser Ile Ala Ala Ala Glu Asp Val Met Ile Val Ser Ala
                20                  25                  30

TCC GGC TAT GAG AAA AAG CTG ACT AAC GCA GCC GCC AGT GTT TCT GTG     144
Ser Gly Tyr Glu Lys Lys Leu Thr Asn Ala Ala Ala Ser Val Ser Val
            35                  40                  45

ATT AGC CAG GAG GAA TTG CAG TCC AGC CAG TAC CAC GAT CTG GCG GAG     192
Ile Ser Gln Glu Glu Leu Gln Ser Ser Gln Tyr His Asp Leu Ala Glu
50                  55                  60

GCT CTG AGA TCA GTA GAG GGT GTG GAT GTT GAA AGT GGT ACG GGT AAA     240
Ala Leu Arg Ser Val Glu Gly Val Asp Val Glu Ser Gly Thr Gly Lys
65                  70                  75                  80

ACC GGA GGG CTG GAA ATC AGC ATC CGA GGA ATG CCA GCC AGT TAC ACG     288
Thr Gly Gly Leu Glu Ile Ser Ile Arg Gly Met Pro Ala Ser Tyr Thr
                85                  90                  95

CTG ATA CTG ATT GAT GGT GTT CGT CAG GGC GGA AGC AGT GAC GTG ACT     336
Leu Ile Leu Ile Asp Gly Val Arg Gln Gly Gly Ser Ser Asp Val Thr
            100                 105                 110

CCC AAC GGT TTT TCT GCC ATG AAT ACC GGG TTC ATG CCC CCT CTG GCC     384
Pro Asn Gly Phe Ser Ala Met Asn Thr Gly Phe Met Pro Pro Leu Ala
        115                 120                 125

GCC ATT GAG CGT ATT GAG GTT ATC AGG GGG CCG ATG TCC ACA CTG TAT     432
Ala Ile Glu Arg Ile Glu Val Ile Arg Gly Pro Met Ser Thr Leu Tyr
    130                 135                 140

GGC TCT GAT GCG ATG GGC GGT GTG GTG AAT ATC ATT ACC AGA AAG AAT     480
Gly Ser Asp Ala Met Gly Gly Val Val Asn Ile Ile Thr Arg Lys Asn
145                 150                 155                 160

GCA GAC AAA TGG CTC TCT TCC GTC AAT GCA GGG CTG AAT CTG CAG GAA     528
Ala Asp Lys Trp Leu Ser Ser Val Asn Ala Gly Leu Asn Leu Gln Glu
                165                 170                 175

AGC AAC AAA TGG GGT AAC AGC AGC CAG TTT AAT TTC TGG AGC AGT GGT     576
Ser Asn Lys Trp Gly Asn Ser Ser Gln Phe Asn Phe Trp Ser Ser Gly
            180                 185                 190

CCC CTT GTG GAT GAT TCT GTC AGC CTG CAG GTA CGC GGT AGC ACA CAA     624
Pro Leu Val Asp Asp Ser Val Ser Leu Gln Val Arg Gly Ser Thr Gln
        195                 200                 205

CAG CGT CAG GGT TCA TCG GTC ACA TCA CTG AGC GAT ACA GCA GGC ACG     672
Gln Arg Gln Gly Ser Ser Val Thr Ser Leu Ser Asp Thr Ala Gly Thr
    210                 215                 220

CGT ATT CCT TAT CCC ACG GAG TCA CAG AAT TAT AAT CTT GGT GCA CGT     720
Arg Ile Pro Tyr Pro Thr Glu Ser Gln Asn Tyr Asn Leu Gly Ala Arg
225                 230                 235                 240
```

```
CTT GAC TGG AAG GCG TCG GAG CAG GAT GTG CTC TGG TTT GAT ATG GAT         768
Leu Asp Trp Lys Ala Ser Glu Gln Asp Val Leu Trp Phe Asp Met Asp
            245                 250                 255

ACC ACC CGG CAG CGT TAT GAT AAC CGG GAT GGG CAA CTG GGG AGT CTG         816
Thr Thr Arg Gln Arg Tyr Asp Asn Arg Asp Gly Gln Leu Gly Ser Leu
        260                 265                 270

ACG GGG GGA TAT GAC CGG ACC CTG CGC TAT GAG CGA AAC AAA ATT TCA         864
Thr Gly Gly Tyr Asp Arg Thr Leu Arg Tyr Glu Arg Asn Lys Ile Ser
            275                 280                 285

GCT GGC TAT GAT CAT ACT TTC ACC TTC GGA ACA TGG AAA TCG TAT CTG         912
Ala Gly Tyr Asp His Thr Phe Thr Phe Gly Thr Trp Lys Ser Tyr Leu
        290                 295                 300

AAC TGG AAC GAG ACA GAA AAT AAA GGT CGT GAG CTT GTA CGC AGT GTA         960
Asn Trp Asn Glu Thr Glu Asn Lys Gly Arg Glu Leu Val Arg Ser Val
305                 310                 315                 320

CTG AAG CGC GAC AAA TGG GGG CTT GCC GGT CAG CCG CGG GAG CTT AAG        1008
Leu Lys Arg Asp Lys Trp Gly Leu Ala Gly Gln Pro Arg Glu Leu Lys
            325                 330                 335

GAA TCG AAC CTT ATC CTG AAT TCA TTA CTG CTT ACC CCT CTG GGA GAA        1056
Glu Ser Asn Leu Ile Leu Asn Ser Leu Leu Leu Thr Pro Leu Gly Glu
        340                 345                 350

TCT CAT CTG GTT ACG GTG GGG GGC GAG TTT CAG AGC TCG TCC ATG AAA        1104
Ser His Leu Val Thr Val Gly Gly Glu Phe Gln Ser Ser Ser Met Lys
            355                 360                 365

GAC GGA GTT GTC CTT GCC AGC ACA GGT GAA ACT TTC CGG CAG AAA AGC        1152
Asp Gly Val Val Leu Ala Ser Thr Gly Glu Thr Phe Arg Gln Lys Ser
        370                 375                 380

TGG TCG GTA TTT GCT GAG GAT GAG TGG CAT CTC ACG GAT GCA CTT GCG        1200
Trp Ser Val Phe Ala Glu Asp Glu Trp His Leu Thr Asp Ala Leu Ala
385                 390                 395                 400

CTG ACT GCG GGC AGC CGC TAT GAA CAT CAT GAG CAA TTC GGG GGA CAC        1248
Leu Thr Ala Gly Ser Arg Tyr Glu His His Glu Gln Phe Gly Gly His
            405                 410                 415

TTC AGT CCG CGT GCA TAT CTG GTC TGG GAT GTG GCA GAT GCC TGG ACG        1296
Phe Ser Pro Arg Ala Tyr Leu Val Trp Asp Val Ala Asp Ala Trp Thr
        420                 425                 430

CTG AAA GGC GGT GTG ACC ACG GGA TAT AAG GCA CCC AGA ATG GGG CAG        1344
Leu Lys Gly Gly Val Thr Thr Gly Tyr Lys Ala Pro Arg Met Gly Gln
            435                 440                 445

CTA CAT AAA GGG ATT AGT GGT GTG TCC GGG CAG GGA AAA ACA AAT CTA        1392
Leu His Lys Gly Ile Ser Gly Val Ser Gly Gln Gly Lys Thr Asn Leu
        450                 455                 460

CTT GGT AAC CCC GAC CTG AAG CCG GAA GAG AGC GTC AGT TAT GAG GCT        1440
Leu Gly Asn Pro Asp Leu Lys Pro Glu Glu Ser Val Ser Tyr Glu Ala
465                 470                 475                 480

GGG GTG TAT TAC GAT AAC CCC GCC GGT CTG AAT GCC AAT GTC ACA GGT        1488
Gly Val Tyr Tyr Asp Asn Pro Ala Gly Leu Asn Ala Asn Val Thr Gly
            485                 490                 495

TTT ATG ACT GAC TTC TCC AAC AAG ATT GTC TCT TAT TCC ATA AAT GAT        1536
Phe Met Thr Asp Phe Ser Asn Lys Ile Val Ser Tyr Ser Ile Asn Asp
        500                 505                 510

AAC ACC AAT AGC TAT GTA AAC AGC GGA AAG GCC CGG TTG CAC GGT GTG        1584
Asn Thr Asn Ser Tyr Val Asn Ser Gly Lys Ala Arg Leu His Gly Val
            515                 520                 525

GAA TTT GCC GGC ACA TTG CCG CTG TGG TCA GAG GAT GTC ACG CTG TCA        1632
Glu Phe Ala Gly Thr Leu Pro Leu Trp Ser Glu Asp Val Thr Leu Ser
        530                 535                 540

CTG AAT TAC ACC TGG ACC CGA AGT GAA CAA CGT GAT GGT GAT AAC AAA        1680
Leu Asn Tyr Thr Trp Thr Arg Ser Glu Gln Arg Asp Gly Asp Asn Lys
545                 550                 555                 560
```

-continued

```
GGT GCG CCG CTG AGT TAT ACC CCT GAA CAC ATG GTG AAT GCG AAA CTG      1728
Gly Ala Pro Leu Ser Tyr Thr Pro Glu His Met Val Asn Ala Lys Leu
                565                 570                 575

AAC TGG CAG ATC ACC GAA GAG GTG GCA TCA TGG CTG GGT GCC CGT TAT      1776
Asn Trp Gln Ile Thr Glu Glu Val Ala Ser Trp Leu Gly Ala Arg Tyr
                580                 585                 590

CGC GGG AAA ACA CCA CGT TTC ACC CAG AAT TAT TCG TCA CTG AGC GCT      1824
Arg Gly Lys Thr Pro Arg Phe Thr Gln Asn Tyr Ser Ser Leu Ser Ala
                595                 600                 605

GTA CAG AAG AAA GTG TAT GAT GAG AAA GGA GAA TAC CTG AAA GCC TGG      1872
Val Gln Lys Lys Val Tyr Asp Glu Lys Gly Glu Tyr Leu Lys Ala Trp
    610                 615                 620

ACG GTG GTG GAT GCA GGT CTG TCG TGG AAG ATG ACG GAT GCC CTG ACG      1920
Thr Val Val Asp Ala Gly Leu Ser Trp Lys Met Thr Asp Ala Leu Thr
625                 630                 635                 640

CTG AAT GCT GCG GTG AAT AAC CTG CTC AAC AAG GAT TAC AGT GAC GTG      1968
Leu Asn Ala Ala Val Asn Asn Leu Leu Asn Lys Asp Tyr Ser Asp Val
                645                 650                 655

AGC CTG TAC AGT GCC GGT AAG AGT ACG CTG TAT GCC GGT GAT TAC TTC      2016
Ser Leu Tyr Ser Ala Gly Lys Ser Thr Leu Tyr Ala Gly Asp Tyr Phe
                660                 665                 670

CAG ACG GGA TCA TCA ACA ACA GGA TAT GTG ATA CCT GAG CGA AAT TAC      2064
Gln Thr Gly Ser Ser Thr Thr Gly Tyr Val Ile Pro Glu Arg Asn Tyr
                675                 680                 685

TGG ATG TCG CTG AAC TAT CAG TTC TGA                                   2091
Trp Met Ser Leu Asn Tyr Gln Phe
690                 695

(2) INFORMATION FOR SEQ ID NO:5:

(i) SEQUENCE CHARACTERISTICS:
         (A) LENGTH: 696 amino acids
         (B) TYPE: amino acid
         (D) TOPOLOGY: linear (ii) MOLECULE TYPE: protein (xi) SEQUENCE DESCRIPTION: SEQ ID NO:5:

Met Arg Ile Thr Thr Leu Ala Ser Val Val Ile Pro Cys Leu Gly Phe
 1               5                  10                  15

Ser Ala Ser Ser Ile Ala Ala Ala Glu Asp Val Met Ile Val Ser Ala
                20                  25                  30

Ser Gly Tyr Glu Lys Lys Leu Thr Asn Ala Ala Ala Ser Val Ser Val
             35                  40                  45

Ile Ser Gln Glu Glu Leu Gln Ser Ser Gln Tyr His Asp Leu Ala Glu
         50                  55                  60

Ala Leu Arg Ser Val Glu Gly Val Asp Val Glu Ser Gly Thr Gly Lys
65                  70                  75                  80

Thr Gly Gly Leu Glu Ile Ser Ile Arg Gly Met Pro Ala Ser Tyr Thr
                85                  90                  95

Leu Ile Leu Ile Asp Gly Val Arg Gln Gly Ser Ser Asp Val Thr
             100                 105                 110

Pro Asn Gly Phe Ser Ala Met Asn Thr Gly Phe Met Pro Pro Leu Ala
         115                 120                 125

Ala Ile Glu Arg Ile Glu Val Ile Arg Gly Pro Met Ser Thr Leu Tyr
    130                 135                 140

Gly Ser Asp Ala Met Gly Gly Val Val Asn Ile Ile Thr Arg Lys Asn
145                 150                 155                 160
```

-continued

```
Ala Asp Lys Trp Leu Ser Ser Val Asn Ala Gly Leu Asn Leu Gln Glu
            165                 170                 175

Ser Asn Lys Trp Gly Asn Ser Ser Gln Phe Asn Phe Trp Ser Ser Gly
            180                 185                 190

Pro Leu Val Asp Asp Ser Val Ser Leu Gln Val Arg Gly Ser Thr Gln
            195                 200                 205

Gln Arg Gln Gly Ser Ser Val Thr Ser Leu Ser Asp Thr Ala Gly Thr
210                 215                 220

Arg Ile Pro Tyr Pro Thr Glu Ser Gln Asn Tyr Asn Leu Gly Ala Arg
225                 230                 235                 240

Leu Asp Trp Lys Ala Ser Glu Gln Asp Val Leu Trp Phe Asp Met Asp
            245                 250                 255

Thr Thr Arg Gln Arg Tyr Asp Asn Arg Asp Gly Gln Leu Gly Ser Leu
            260                 265                 270

Thr Gly Gly Tyr Asp Arg Thr Leu Arg Tyr Glu Arg Asn Lys Ile Ser
            275                 280                 285

Ala Gly Tyr Asp His Thr Phe Thr Phe Gly Thr Trp Lys Ser Tyr Leu
290                 295                 300

Asn Trp Asn Glu Thr Glu Asn Lys Gly Arg Glu Leu Val Arg Ser Val
305                 310                 315                 320

Leu Lys Arg Asp Lys Trp Gly Leu Ala Gly Gln Pro Arg Glu Leu Lys
            325                 330                 335

Glu Ser Asn Leu Ile Leu Asn Ser Leu Leu Leu Thr Pro Leu Gly Glu
            340                 345                 350

Ser His Leu Val Thr Val Gly Gly Glu Phe Gln Ser Ser Ser Met Lys
            355                 360                 365

Asp Gly Val Val Leu Ala Ser Thr Gly Glu Thr Phe Arg Gln Lys Ser
370                 375                 380

Trp Ser Val Phe Ala Glu Asp Glu Trp His Leu Thr Asp Ala Leu Ala
385                 390                 395                 400

Leu Thr Ala Gly Ser Arg Tyr Glu His His Glu Gln Phe Gly Gly His
            405                 410                 415

Phe Ser Pro Arg Ala Tyr Leu Val Trp Asp Val Ala Asp Ala Trp Thr
            420                 425                 430

Leu Lys Gly Gly Val Thr Thr Gly Tyr Lys Ala Pro Arg Met Gly Gln
            435                 440                 445

Leu His Lys Gly Ile Ser Gly Val Ser Gly Gln Gly Lys Thr Asn Leu
            450                 455                 460

Leu Gly Asn Pro Asp Leu Lys Pro Glu Glu Ser Val Ser Tyr Glu Ala
465                 470                 475                 480

Gly Val Tyr Tyr Asp Asn Pro Ala Gly Leu Asn Ala Asn Val Thr Gly
            485                 490                 495

Phe Met Thr Asp Phe Ser Asn Lys Ile Val Ser Tyr Ser Ile Asn Asp
            500                 505                 510

Asn Thr Asn Ser Tyr Val Asn Ser Gly Lys Ala Arg Leu His Gly Val
            515                 520                 525

Glu Phe Ala Gly Thr Leu Pro Leu Trp Ser Glu Asp Val Thr Leu Ser
530                 535                 540

Leu Asn Tyr Thr Trp Thr Arg Ser Glu Gln Arg Asp Gly Asp Asn Lys
545                 550                 555                 560

Gly Ala Pro Leu Ser Tyr Thr Pro Glu His Met Val Asn Ala Lys Leu
            565                 570                 575

Asn Trp Gln Ile Thr Glu Glu Val Ala Ser Trp Leu Gly Ala Arg Tyr
```

-continued

```
                580                 585                 590
Arg Gly Lys Thr Pro Arg Phe Thr Gln Asn Tyr Ser Ser Leu Ser Ala
            595                 600                 605

Val Gln Lys Lys Val Tyr Asp Glu Lys Gly Tyr Leu Lys Ala Trp
610                 615                 620

Thr Val Val Asp Ala Gly Leu Ser Trp Lys Met Thr Asp Ala Leu Thr
625                 630                 635                 640

Leu Asn Ala Ala Val Asn Asn Leu Leu Asn Lys Asp Tyr Ser Asp Val
            645                 650                 655

Ser Leu Tyr Ser Ala Gly Lys Ser Thr Leu Tyr Ala Gly Asp Tyr Phe
            660                 665                 670

Gln Thr Gly Ser Ser Thr Thr Gly Tyr Val Ile Pro Glu Arg Asn Tyr
            675                 680                 685

Trp Met Ser Leu Asn Tyr Gln Phe
    690                 695
```

(2) INFORMATION FOR SEQ ID NO:6:

(i) SEQUENCE CHARACTERISTICS:
       (A) LENGTH: 652 amino acids
       (B) TYPE: amino acid
       (C) TOPOLOGY: linear (ii) MOLECULE TYPE: protein
       (A) DESCRIPTION: Vibrio cholerae IrgA amino acid sequence (iii) HYPOTHETICAL: NO (vi) ORIGINAL SOURCE:
       (A) ORGANISM: Vibrio Cholerae (xi) SEQUENCE DESCRIPTION: SEQ ID NO:6:

```
Met Ser Arg Phe Asn Pro Ser Pro Val Ser Leu Ser Val Thr Leu Gly
1               5                   10                  15

Leu Met Phe Ser Ala Ser Ala Phe Ala Gln Asp Ala Thr Lys Thr Asp
            20                  25                  30

Glu Thr Met Val Val Thr Ala Ala Gly Tyr Ala Gln Val Ile Gln Asn
        35                  40                  45

Ala Pro Ala Ser Ile Ser Val Ile Ser Arg Glu Asp Leu Glu Ser Arg
    50                  55                  60

Tyr Tyr Arg Asp Val Thr Asp Ala Leu Lys Ser Val Pro Gly Val Thr
65                  70                  75                  80

Val Thr Gly Gly Gly Asp Thr Thr Asp Ile Ser Ile Arg Gly Met Gly
                85                  90                  95

Ser Asn Tyr Thr Leu Ile Leu Val Asp Gly Lys Arg Gln Thr Ser Arg
            100                 105                 110

Gln Thr Arg Pro Asn Ser Asp Gly Pro Gly Ile Glu Gln Gly Trp Leu
        115                 120                 125

Pro Pro Leu Gln Ala Ile Glu Arg Ile Glu Val Ile Arg Gly Pro Met
    130                 135                 140

Ser Thr Leu Tyr Gly Ser Asp Ala Ile Gly Gly Val Ile Asn Ile Ile
145                 150                 155                 160

Thr Arg Lys Asp Gln Gln Gln Trp Ser Gly Asn Val Gln Leu Ser Thr
                165                 170                 175

Val Val Gln Glu Asn Arg Ala Ser Gly Asp Glu Gln Ser Ala Asn Phe
            180                 185                 190

Phe Val Thr Gly Pro Leu Ser Asp Ala Leu Ser Leu Gln Val Tyr Gly
        195                 200                 205
```

```
Gln Thr Thr Gln Arg Asp Glu Asp Glu Ile Glu His Gly Tyr Gly Asp
    210                 215                 220

Lys Ser Leu Arg Ser Leu Thr Ser Lys Leu Asn Tyr Gln Leu Asn Pro
225                 230                 235                 240

Asp His Gln Leu Gln Leu Glu Ala Gly Val Ser Ala Gln Asp Arg Glu
                245                 250                 255

Asn Asn Val Gly Lys Ser Ala Gln Ser Ser Gly Cys Arg Gly Thr Cys
            260                 265                 270

Ser Asn Thr Asp Asn Gln Tyr Arg Arg Asn His Val Ala Val Ser His
        275                 280                 285

Gln Gly Asp Trp Gln Gly Val Gly Gln Ser Asp Thr Tyr Leu Gln Tyr
    290                 295                 300

Glu Glu Asn Thr Asn Lys Ser Arg Glu Met Ser Ile Asp Asn Thr Val
305                 310                 315                 320

Phe Lys Ser Thr Leu Val Ala Pro Ile Gly Glu His Met Leu Ser Phe
                325                 330                 335

Gly Val Glu Gly Lys His Glu Ser Leu Glu Asp Lys Thr Ser Asn Lys
            340                 345                 350

Ile Ser Ser Arg Thr His Ile Ser Asn Thr Gln Trp Ala Gly Phe Ile
        355                 360                 365

Glu Asp Glu Trp Ala Leu Ala Glu Gln Phe Arg Leu Thr Phe Gly Gly
    370                 375                 380

Arg Leu Asp His Asp Lys Asn Tyr Gly Ser His Phe Ser Pro Arg Val
385                 390                 395                 400

Tyr Gly Val Trp Asn Leu Asp Pro Leu Trp Thr Val Lys Gly Gly Val
                405                 410                 415

Ser Thr Gly Phe Arg Ala Pro Gln Leu Arg Glu Val Thr Pro Asp Trp
            420                 425                 430

Gly Gln Val Ser Gly Gly Asn Ile Tyr Gly Asn Pro Asp Leu Gln
        435                 440                 445

Pro Glu Thr Ser Ile Asn Lys Glu Leu Ser Leu Met Tyr Ser Thr Gly
    450                 455                 460

Ser Gly Leu Ala Ala Ser Leu Thr Ala Phe His Asn Asp Phe Lys Asp
465                 470                 475                 480

Lys Ile Thr Arg Val Ala Cys Pro Ala Asn Ile Cys Thr Ala Gly Pro
                485                 490                 495

Asn Gln Trp Gly Ala Thr Pro Tyr Arg Val Asn Ile Asp Glu Ala
            500                 505                 510

Glu Thr Tyr Gly Ala Glu Ala Thr Leu Ser Leu Pro Ile Thr Glu Ser
        515                 520                 525

Val Glu Leu Ser Ser Ser Tyr Thr Tyr Thr His Ser Glu Gln Lys Ser
    530                 535                 540

Gly Asn Phe Ala Gly Arg Pro Leu Leu Gln Leu Pro Lys His Leu Phe
545                 550                 555                 560

Asn Ala Asn Leu Ser Trp Gln Thr Thr Asp Arg Leu Asn Ser Trp Ala
                565                 570                 575

Asn Leu Asn Tyr Arg Gly Lys Glu Met Gln Pro Glu Gly Gly Ala Ser
            580                 585                 590

Asn Asp Asp Phe Ile Ala Pro Ser Tyr Thr Phe Ile Asp Thr Gly Val
        595                 600                 605

Thr Tyr Ala Leu Thr Asp Thr Ala Thr Ile Lys Ala Ala Val Tyr Asn
    610                 615                 620
```

```
Leu Phe Asp Gln Glu Val Asn Tyr Ala Glu Tyr Gly Tyr Val Glu Asp
625                 630                 635                 640

Gly Arg Arg Tyr Trp Leu Gly Leu Asp Ile Ala Phe
                645                 650

(2) INFORMATION FOR SEQ ID NO:7:

(i) SEQUENCE CHARACTERISTICS:
        (A) LENGTH: 663 amino acids
        (B) TYPE: amino acid
        (C) TOPOLOGY: linear (ii) MOLECULE TYPE: protein
        (A) DESCRIPTION: E. coli CirA protein amino acid sequence (iii) HYPOTHETICAL: NO (vi) ORIGINAL SOURCE:
        (A) ORGANISM: Escherichia Coli (xi) SEQUENCE DESCRIPTION: SEQ ID NO:7:

Met Phe Arg Leu Asn Pro Phe Val Arg Val Gly Leu Cys Leu Ser Ala
1               5                   10                  15

Ile Ser Cys Ala Trp Pro Val Leu Ala Val Asp Asp Asp Gly Glu Thr
                20                  25                  30

Met Val Val Thr Ala Ser Ser Val Glu Gln Asn Leu Lys Asp Ala Pro
            35                  40                  45

Ala Ser Ile Ser Val Ile Thr Gln Glu Asp Leu Gln Arg Lys Pro Val
        50                  55                  60

Gln Asn Leu Lys Asp Val Leu Lys Glu Val Pro Gly Val Gln Leu Thr
65                  70                  75                  80

Asn Glu Gly Asp Asn Arg Lys Gly Val Ser Ile Arg Gly Leu Asp Ser
                85                  90                  95

Ser Tyr Thr Leu Ile Leu Val Asp Gly Lys Arg Val Asn Ser Arg Asn
                100                 105                 110

Ala Val Phe Arg His Asn Asp Phe Asp Leu Asn Trp Ile Pro Val Asp
            115                 120                 125

Ser Ile Glu Arg Ile Glu Val Val Arg Gly Pro Met Ser Ser Leu Tyr
        130                 135                 140

Gly Ser Asp Ala Leu Gly Gly Val Val Asn Ile Ile Thr Lys Lys Ile
145                 150                 155                 160

Gly Gln Lys Trp Ser Gly Thr Val Thr Val Asp Thr Thr Ile Gln Glu
                165                 170                 175

His Arg Asp Arg Gly Asp Thr Tyr Asn Gly Gln Phe Phe Thr Ser Gly
                180                 185                 190

Pro Leu Ile Asp Gly Val Leu Gly Met Lys Ala Tyr Gly Ser Leu Ala
            195                 200                 205

Lys Arg Glu Lys Asp Asp Pro Gln Asn Ser Thr Thr Thr Asp Thr Gly
210                 215                 220

Glu Thr Pro Arg Ile Glu Gly Phe Ser Ser Arg Asp Gly Asn Val Glu
225                 230                 235                 240

Phe Ala Trp Thr Pro Asn Gln Asn His Asp Phe Thr Ala Gly Tyr Gly
                245                 250                 255

Phe Asp Arg Gln Asp Arg Asp Ser Asp Ser Leu Asp Lys Asn Arg Leu
            260                 265                 270

Glu Arg Gln Asn Tyr Ser Val Ser His Asn Gly Arg Trp Asp Tyr Gly
        275                 280                 285

Thr Ser Glu Leu Lys Tyr Tyr Gly Glu Lys Val Glu Asn Lys Asn Pro
```

-continued

```
                290                 295                 300
Gly Asn Ser Ser Pro Ile Thr Ser Glu Ser Asn Thr Val Asp Gly Lys
305                 310                 315                 320

Tyr Thr Leu Pro Leu Thr Ala Ile Asn Gln Phe Leu Thr Val Gly Gly
                325                 330                 335

Glu Trp Arg His Asp Lys Leu Ser Asp Ala Val Asn Leu Thr Gly Gly
                340                 345                 350

Thr Ser Ser Lys Thr Ser Ala Ser Gln Tyr Ala Leu Phe Val Glu Asp
                355                 360                 365

Glu Trp Arg Ile Phe Glu Pro Leu Ala Leu Thr Thr Gly Val Arg Met
370                 375                 380

Asp Asp His Glu Thr Tyr Gly Glu His Trp Ser Pro Arg Ala Tyr Leu
385                 390                 395                 400

Val Tyr Asn Ala Thr Asp Thr Val Thr Val Lys Gly Gly Trp Ala Thr
                405                 410                 415

Ala Phe Lys Ala Pro Ser Leu Leu Gln Leu Ser Pro Asp Trp Thr Ser
                420                 425                 430

Asn Ser Cys Arg Gly Ala Cys Lys Ile Val Gly Ser Pro Asp Leu Lys
                435                 440                 445

Pro Glu Thr Ser Glu Ser Trp Glu Leu Gly Leu Tyr Tyr Met Gly Glu
450                 455                 460

Glu Gly Trp Leu Glu Gly Val Glu Ser Ser Val Thr Val Phe Arg Asn
465                 470                 475                 480

Asp Val Lys Asp Arg Ile Ser Ile Ser Arg Thr Ser Asp Val Asn Ala
                485                 490                 495

Ala Pro Gly Tyr Gln Asn Phe Val Gly Phe Glu Thr Gly Ala Asn Gly
                500                 505                 510

Arg Arg Ile Pro Val Phe Ser Tyr Tyr Asn Val Asn Lys Ala Arg Asn
                515                 520                 525

Gln Gly Val Glu Thr Glu Leu Lys Ile Pro Phe Asn Asp Glu Trp Lys
530                 535                 540

Leu Ser Ile Asn Tyr Thr Tyr Asn Asp Gly Arg Asp Val Ser Asn Gly
545                 550                 555                 560

Glu Asn Lys Pro Leu Ser Asp Leu Pro Phe His Leu Ala Leu Glu Asp
                565                 570                 575

Trp Ser Phe Tyr Val Ser Gly His Tyr Thr Gly Gln Lys Arg Ala Asp
                580                 585                 590

Ser Ala Thr Ala Lys Thr Pro Gly Gly Tyr Thr Ile Trp Asn Thr Gly
                595                 600                 605

Ala Ala Trp Gln Val Thr Lys Asp Val Lys Leu Arg Ala Gly Val Leu
610                 615                 620

Asn Leu Gly Asp Lys Thr Ala Asn Gly Thr Leu Asp Trp Lys Pro Asp
625                 630                 635                 640

Leu Ser Arg Asp Asp Tyr Ser Tyr Asn Glu Asp Gly Arg Arg Tyr Phe
                645                 650                 655

Met Ala Val Asp Tyr Arg Phe
                660
```

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (vi) ORIGINAL SOURCE:
             (A) ORGANISM: Escherichia coli O157:H7
             (B) STRAIN: 86-24 NALR (xi) SEQUENCE DESCRIPTION: SEQ ID NO:8:

GGGGATCCAA TTCTGGCATG CCGAGGCAGT CG                                             32

(2) INFORMATION FOR SEQ ID NO:9:

(i) SEQUENCE CHARACTERISTICS:
             (A) LENGTH: 33 base pairs
             (B) TYPE: nucleic acid
             (C) STRANDEDNESS: single
             (D) TOPOLOGY: linear (ii) MOLECULE TYPE: other nucleic acid (ii) HYPOTHETICAL: NO (iv) ANTI-SENSE: NO (vi) ORIGINAL SOURCE:
             (A) ORGANISM: Escherichia coli O157:H7
             (B) STRAIN: 86-24 NALR (xi) SEQUENCE DESCRIPTION: SEQ ID NO:9:

GGACCGCCTT GTCACCGTTG CTCTTAGATC TGG                                            33

(2) INFORMATION FOR SEQ ID NO:10:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: NO (vi) ORIGINAL SOURCE:
             (A) ORGANISM: Escherichia coli O157:H7
             (B) STRAIN: 86-24NALR (xi) SEQUENCE DESCRIPTION: SEQ ID NO:10:

GGAAGGATCC CCGAACACGC CATACGGATA GCTG                                           34

(2) INFORMATION FOR SEQ ID NO:11:

(i) SEQUENCE CHARACTERISTICS:
             (A) LENGTH: 35 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: NO (vi) ORIGINAL SOURCE:
             (A) ORGANISM: Escherichia coli O157:H7
             (B) STRAIN: 86-24NALR (xi) SEQUENCE DESCRIPTION: SEQ ID NO:11:

GCAACGGTGA CGTTGAGGAC CGCCAGATCT AAAGG                                35

(2) INFORMATION FOR SEQ ID NO:12:

(i) SEQUENCE CHARACTERISTICS:
              (A) LENGTH: 300 base pairs
              (B) TYPE: nucleic acid
              (C) STRANDEDNESS: single
              (D) TOPOLOGY: linear (ii) MOLECULE TYPE: DNA (genomic)
              (A) DESCRIPTION: Genomic DNA fragment described on page 10
                  of the specification (iii) HYPOTHETICAL: NO (iv) ANTI-SENSE: NO (vi) ORIGINAL SOURCE:
              (A) ORGANISM: Escherichia coli O157:H7
              (B) STRAIN: A5,F4,N11

(xi) SEQUENCE DESCRIPTION: SEQ ID NO:12:

ATGGAAGCAG CAAATTTAAG TCCTTCTGGT GCAGTAATGC CGCTGGCGAC CTCACTCAGT       60

GGAAATAACT CAGTGGATGA GAAGACAGGA GTGATTAAAC CAGAAAATGG AACAAATCGC      120

ACCGTTAGAG TTATAGCCGG ATTAGCACTT ACCACTACGG CTCTGGCAGC TCTAGGTACA      180

GGTATTGCAG CGGCATGCTC GGAGACGAGC AGCACAGAAT ACTTAGCCCT GGGTATTACT      240

TCTGGCGTAC TAGGTACTCT TACTGCGGTT GGCGGTGCAT TAGCGATGAA ATATGCCTAA      300